(12) United States Patent
Giannini et al.

(10) Patent No.: US 10,993,888 B2
(45) Date of Patent: May 4, 2021

(54) FLUORESCENT NANOPARTICLE COMPOSITIONS FOR DENTAL BONDED RESTORATIONS

(71) Applicant: Augusta University Research Institute, Inc., Augusta, GA (US)

(72) Inventors: Marcelo Giannini, Campinas (BR); Rafael Rocha Pacheco, Campinas (BR); Frederick Allen Rueggeberg, Augusta, GA (US); Jorge Rodrigo Soto Montero, Campinas (BR); Eduardo David Martinez, Campinas (BR); Ali Francisco Garcia Flores, Campinas (BR); Ailla Carla Rocha Acosta Lancellotti, Campinas (BR); Guilherme Gorgen Lesseux, Campinas (BR); Carlos Rettori, Campinas (BR); Ricardo Rodrigues Urbano, Campinas (BR)

(73) Assignee: AUGUSTA UNIVERSITY RESEARCH INSTITUTE, INC., Augusta, GA (US)

(*) Notice: Subject to any disclaimer, the term of this patent is extended or adjusted under 35 U.S.C. 154(b) by 22 days.

(21) Appl. No.: 16/228,014

(22) Filed: Dec. 20, 2018

(65) Prior Publication Data

US 2019/0183742 A1 Jun. 20, 2019

Related U.S. Application Data

(60) Provisional application No. 62/608,254, filed on Dec. 20, 2017, provisional application No. 62/608,271, filed on Dec. 20, 2017.

(51) Int. Cl.
*A61K 6/17* (2020.01)
*A61K 6/842* (2020.01)
(Continued)

(52) U.S. Cl.
CPC ............... *A61K 6/17* (2020.01); *A61K 6/842* (2020.01); *A61K 6/887* (2020.01); *C01F 17/265* (2020.01); *C09K 11/7773* (2013.01); *C08L 33/02* (2013.01)

(58) Field of Classification Search
CPC ............. C09K 11/7773; C01F 17/265; A61K 6/00–90; C08L 33/02
See application file for complete search history.

(56) References Cited

U.S. PATENT DOCUMENTS 9,675,435 B2 6/2017 Karazivan
2009/0130031 A1* 5/2009 Herman ............... B82Y 5/00
424/49

(Continued)

FOREIGN PATENT DOCUMENTS

CA 2875502 1/2018

OTHER PUBLICATIONS

Mai et al., "High-Quality Sodium Rare-Earth Fluoride Nanocrystals: Controlled Synthesis and Optical Properties," J. Am. Chem. Soc. 128,6426-6436 (2006).*

(Continued)

*Primary Examiner* — Kregg T Brooks
(74) *Attorney, Agent, or Firm* — Smith, Gambrell & Russell

(57) ABSTRACT

Fluorescent nanoparticle compositions and methods of used for dental bonded restorations are provided herein.

9 Claims, 21 Drawing Sheets

(51) Int. Cl.
*A61K 6/887* (2020.01)
*C01F 17/265* (2020.01)
*C09K 11/77* (2006.01)
*C08L 33/02* (2006.01)

(56) References Cited

U.S. PATENT DOCUMENTS

2015/0182321 A1\* 7/2015 Karazivan ............... C09D 5/22
  433/3
2016/0250332 A1  9/2016 Punjabi
2017/0096585 A1  4/2017 Fathi

OTHER PUBLICATIONS

Liu et al., "Monodisperse, size-tunable and highly efficient β-NaYF4:Yb,Er(Tm) up-conversion luminescent nanospheres: controllable synthesis and their surface modifications," J. Mater. Chem. 19, 3546-3553 (2009).\*
Zhang, Hua et al., "Composition Tuning the Upconversion Emission in NaYF4:Yb/Tm Hexaplate Nanocrystals", Nanoscale, 3:963-966 (2011).
Zou, Peng et al., "Up-Conversion Luminescence of NaYF4:Yb3+/Er3+ Nanoparticles Embedded into PVP Nanotubes with Controllable Diameters", J. Phys. Chem. C, 116(9) 5787-5791 (2012).

\* cited by examiner

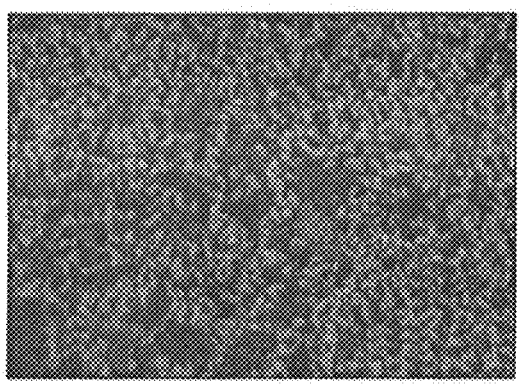
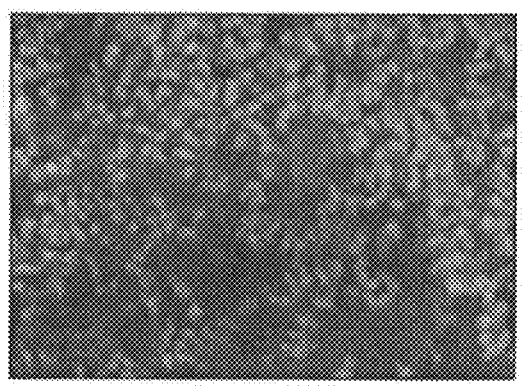
FIG.3A
FIG.3B
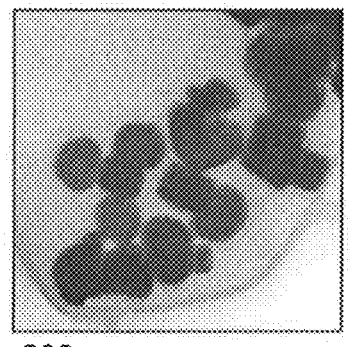
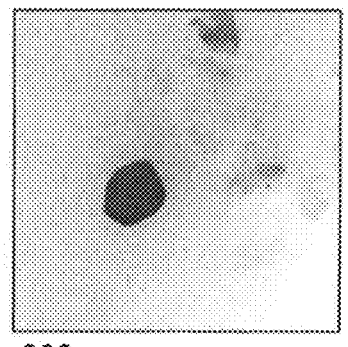
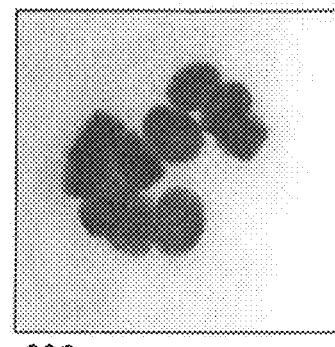
FIG.4A
FIG.4B
FIG.4C
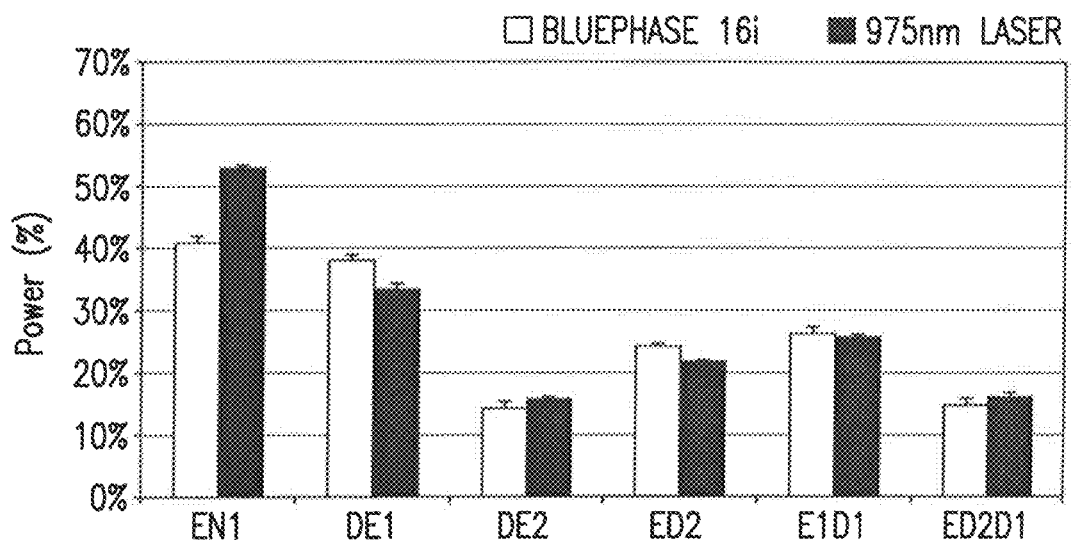
FIG.5

FLUORESCENT NANOPARTICLE COMPOSITIONS FOR DENTAL BONDED RESTORATIONS

CROSS-REFERENCE TO RELATED APPLICATIONS

This application claims benefit of and priority to U.S. Provisional Application Nos. 62/608,254 filed on Dec. 20, 2017, and 62/608,271 filed on Dec. 20, 2017, both of which are incorporated by reference in their entirety.

TECHNICAL FIELD OF THE INVENTION

This invention is generally related to the field of dentistry, more specifically dental restorative material such as resin.

BACKGROUND OF THE INVENTION

Tooth decay, also known as dental caries or cavities, are a breakdown of teeth due to acids produced by specific types of bacteria within the oral cavity. Symptoms of tooth decay include pain and difficulty eating. If left untreated, tooth decay can lead to inflammation of the tissue around the affected tooth, tooth loss, and infection or abscess formation. Treatment for tooth decay includes fluoride, fillings, and crowns. Severe cases may result in a root canal or removal of the affected tooth. The most common way to treat cavities due to tooth decay is through dental restoration, more specifically dental fillings. Dental restoration restores the function, integrity, and morphology of the affected tooth or teeth.

Dental fillings are a routine part of dental care. First, the affected part of the tooth is cleaned and prepared for the filling. This often involves cutting away parts of the tooth to remove dental decay or portions of the tooth that are structurally unsound, leaving behind a hole or empty space in the tooth. The hole is then filled with dental restorative composites. Traditional composite fillings are made of a resin and plastic material that is placed into the cavity while the material is soft, then hardened with a curing light. The placement of composite resins poses many challenges however, light-curing is central to ensuring the success and longevity of the filling. Under-polymerized adhesives and composites risk premature restorative failure due to reduced bond strengths, microleakage, postoperative sensitivity, pulpal toxicity, recurrent caries, color instability, and increased wear and fracture.

When traditional composite resins are cured, the resin at the surface of the tooth is exposed to more light than the resin at the bottom of the cavity, leading to uneven curing time. The resin at the surface of the tooth will begin to cure before the resin at the base of the cavity, causing the resin at the base to pull away from the surface of the tooth. This leads to voids within the filling and can cause tooth pain in the patient. In addition, the voids cause the filling to be less durable, requiring them to be replaced over time.

There is a need for more permanent, durable dental composites for fillings.

It is an object of the invention to provide compositions and methods for permanent, long-lasting dental fillings.

SUMMARY OF THE INVENTION

Nanoparticles containing nanocrystals of $NaYF_4$ doped with rare earth metals such as Er, Yb and Tm and compositions containing the nanoparticles are provided. The nanoparticles exhibit fluorescence properties at specific optical wavelengths. In some embodiments the nanoparticles emit blue light (≈460 nm) or violet light (≈400 nm) when irradiated by an infrared laser of 975 nm., and the emitted light promotes the curing of dental restorative materials. In one embodiment, the nanoparticles have nanocrystals of $NaYF_4$ doped with 69.5% mole of yttrium, 30% mole of ytterbium, and 0.5% mole of thulium, per mole of sodium.

In one embodiment, the nanoparticles have a particle size ranging from 100-200 nm and are added to dental restorative materials in a concentration of approximately 10 or 30% w/w.

Another embodiment provides nanoparticles of $NaYF_4$ doped with rare earth metals such as Er, Yb and Tm, wherein the nanocrystals are functionalized. In one embodiment, the nanocrystals are functionalized with a polymer. In another embodiment, the surface of the nanocrystals is functionalized with polyacrylic acid. The functionalized surface can promote or enhance bonding of the nanoparticles to the dental restorative material. The dental restorative materials can be any one of an adhesive solution, liner, or dental cement. The composition can be a foundation, base, adhesive, restorative composite resin, or dental resin cement.

One embodiment provides a method of making dental restorations including steps of applying a dental restoration composition of nanocrystals of rare earth doped $NaYF_4$ having a polyacrylic acid functionalized surface to an affected area of a tooth in a subject in need thereof and curing the dental restoration composition using infrared light. The infrared light causes the nanoparticles contained in the seeded resin-based dental material to locally emit blue light at a wavelength of 460 nm or 400 nm. In one embodiment, the subject in need thereof has a tooth decay, dental caries, or tooth erosion.

BRIEF DESCRIPTION OF THE DRAWINGS

For a full and complete overview of the subject of this invention, there are shown the figures which are referred to, as follows.

FIGS. 3A-3B are micrographs obtained using scanning electron microscopy (SEM) of the synthesized nanoparticles, where FIG. 3A shows a magnification of ×10,000 and FIG. 3B shows magnification of ×20,000.

FIGS. 4A-4C are micrographs obtained by transmission electron microscopy (TEM) of the synthesized nanoparticles, magnified to ×120.

FIG. 5 graphically depicts the 975 nm laser light transmission and blue light transmission (blue LED dental curing light, Bluephase 16i, Ivoclar Vivadent) through different dental tissue substrates.

FIG. 10A shows total emission, FIG. 10B shows emission between 460-490 nm wavelengths, FIG. 10C shows emission between 440-460 nm wavelengths, and FIG. 10D shows emissions between 350-370 nm wavelength.

FIGS. 19A-19D show the blue emission when the IR light is transmitted through 1 mm of a commercial, resin-based dental composite (EverX, GC Europe), FIGS. 19M-19P show the results when the IR light was shined through 4 mm of this restorative composite material.

DETAILED DESCRIPTION OF THE INVENTION

I. Definitions

Figure 1:
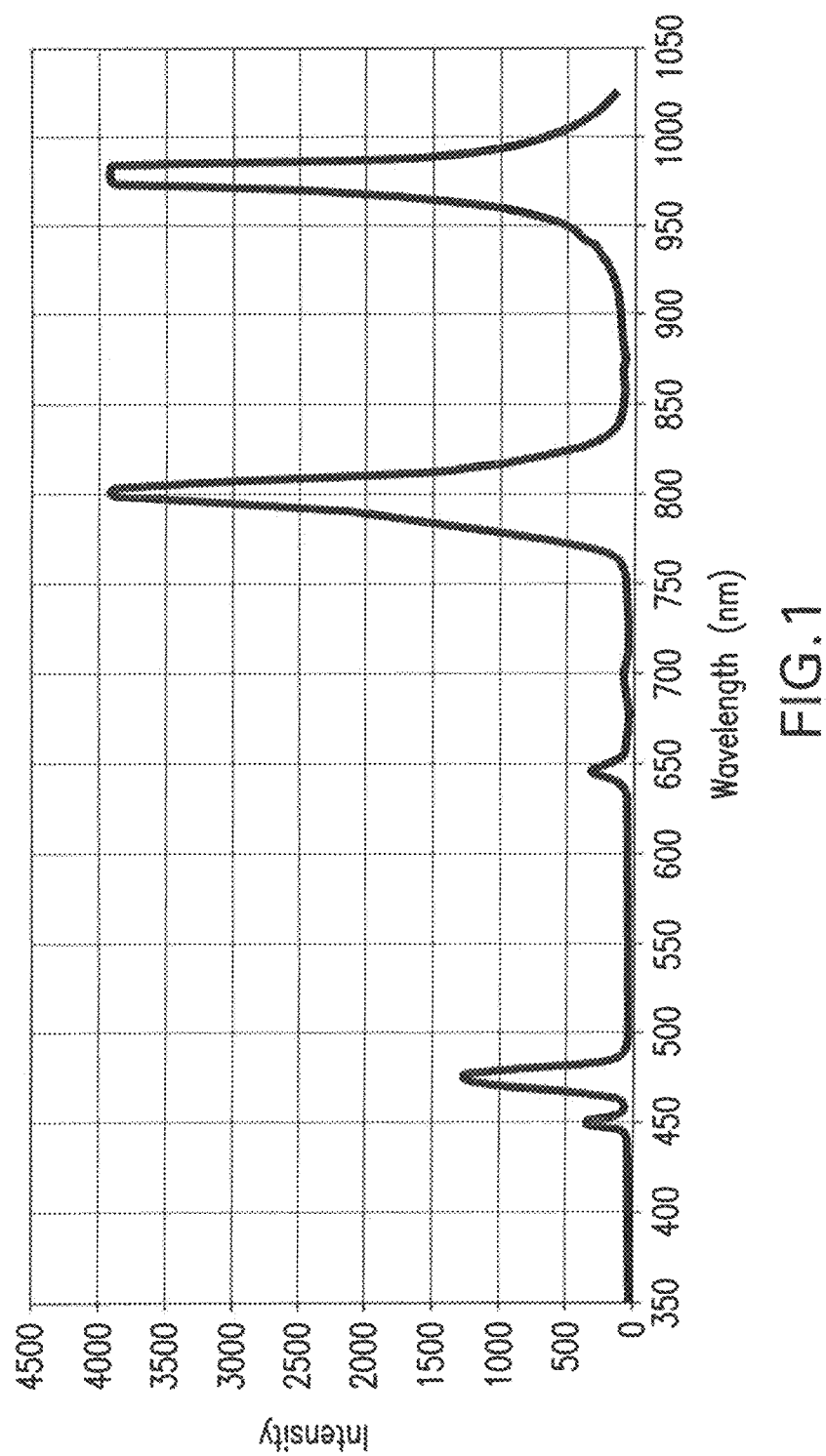
FIG. 1 shows the emission spectrum of the nanoparticle powder when irradiated using the 975 nm IR laser.

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "dental restoration" or "dental filling" refer to a treatment to restore the function, integrity, and morphology of missing tooth structure resulting from caries or external trauma. Common dental problems that require dental restoration include but are not limited to tooth decay, dental caries, or tooth erosion (enamel).

As used herein "dental restorative material" refers to materials used to replace tooth structure loss, usually due to dental caries, tooth wear, and dental trauma. Exemplary dental restorative materials include but are not limited to amalgam, composite resin, glass ionomer cement, and resin modified glass-ionomer cement, cements, and lining materials such as calcium hydroxide, polycarboxylate cement, glass ionomer, and zinc oxide eugenol.

"Direct restoration" refers to the technique of placing a soft or malleable filling into the prepared tooth and building up the tooth. The material is then set and the tooth is restored.

"Indirect restoration" refers to the technique of fabricating the restoration outside of the mouth using dental impressions of the prepared tooth. Common indirect restorations include but are not limited to inlays and onlays, crowns, bridges, and veneers.

II. Nanoparticles for Dental Restorative Compositions

Nanoparticles containing nanocrystals of $NaYF_4$ doped with rare earth metals such as Er, Yb and Tm and compositions containing the nanoparticles are provided herein. The nanoparticles exhibit fluorescence properties at specific optical wavelengths. In some embodiments the nanoparticles emit blue light (≈460 nm) or violet light (≈400 nm) when irradiated by an infrared laser of 975 nm., and the emitted light promotes the curing of dental restorative materials.

The light-curing procedure is an important step in restorative dentistry because it ensures optimal properties of resin-based restorative materials. The restorative materials are light activated, using a wavelength specific for excitation of photoinitiators purposefully compounded into the light-activated dental restorative product.

Amino-associated camphorquinone is the most common photoinitiator system used in resin dental restorative material formulations and is sensitive to blue light (peak absorption at 468 nm). This light and others with shorter wavelengths are highly dispersed in different materials, resulting in a technical limitation for composite resin restoration procedures known as curing depth.

It is recommended that conventional composites be applied in increments that should not exceed 2 mm thick, which increases the clinical time to perform the restorative procedure. The same effect is observed for indirect restorations, because the high frequencies are attenuated when transmitted by the restorative material, which could reduce the degree of conversion and the mechanical properties of resin cements and resin-based restorative materials.

In addition, during polymerization, the free space between monomers is partially lost by the chemical reaction, resulting in a volumetric reduction known as polymerization contraction. This volumetric reduction results in tensions (stresses) that can affect the union area (adhesive-tooth) of the restoration, leading to the formation of marginal crevices, micro-fractures of the enamel, postoperative sensitivity, marginal discoloration, and even secondary caries. The contraction tension is influenced by many factors, including material composition, cavity design, material insertion technique, and photocuring light incident irradiance.

In one embodiment, the disclosed nanoparticle compositions can cure uniformly and do not incur volumetric reduction. The nanoparticles of the present invention reduce the deleterious effects inherent in the polymerization process of resin dental materials (such as conversion degree deficient in deeper portions of dental cavity preparations or through indirect materials as well as problems generated by the polymerization contraction of these materials). In addition, the present invention includes a step of functionalizing the surface of the particles with polyacrylic acid in order to allow the bond between them and the restoring resin.

A. Rare Earth Doped Nanoparticles

The present invention describes nanoparticles having optical fluorescence properties, which comprise nanocrystals of $NaYF_4$ doped with rare earths (Er, Yb, and Tm), in hexagonal format. In one embodiment, the nanocrystals are created from $NaYF_4$ doped with 69.5% mole of yttrium, 30% mole of ytterbium, and 0.5% mole of thulium, per mole of sodium.

During the synthesis of nanoparticles (NPs) of $NaYF_4$ doped with rare earths, the resulting nanocrystals can crystallize in the cubic (a-phase) or hexagonal (β phase) structure, depending on the synthesis method. It is critical to obtain specific phases, because—$NaYF_4$ doped with $Yb^{+3}$ and $Tm^{+3}$ is known to be one of the most efficient materials in the "upconversion" phenomenon ($3.4 \times 10^{-2}$ $cm^2/mWn^{-1}$). The anti-Stokes effect or "upconversion" (UC) violates the basic law of Stokes because the low energy photons can convert molecules into higher energy. These longer wavelengths (such as infrared) have greater penetration through different materials and are converted to shorter wavelengths, such as visible blue light.

In one embodiment, incorporation of nanoparticles that promote UC into dental restorative materials, and in hydrophobic/hydrophilic adhesives applied to the walls of the dental cavity may result in a material that emits blue light in the region where the material is joined to the cavity walls, leading to the monomeric conversion of the restorative composite placed adjacent to it, possibly reducing the limitations of blue light transmission and potential interfacial debonding caused from the curing tension vectors generated by the polymerization contraction.

The crystal size is also critical for UC efficiency because nanoparticles have a much larger surface/volume ratio when compared to larger particles. Thus, the efficiency is relative to the format and is inversely related to the size of NPs. In one embodiment, the nanoparticles have a particle size ranging from 100 to 200 nm. The nanoparticles can have a particle size that is 100, 110, 120, 130, 140, 150, 160, 170, 180, 190, or 200 nm. In one embodiment, the nanocrystals are hexagonal in shape.

In order to allow the bond between them and the restorative resin, the present invention includes a step of functionalizing the surface of the particles with polyacrylic acid, using a hydrophilic fluid resin incorporating 10% nanoparticles (because it is an adhesive resin solution). In one embodiment, the nanoparticles can be functionalized. The nanoparticles can be functionalized with polyacrylic acid. In one embodiment, the polyacrylic acid functionalized surface bonds the nanoparticles to the dental restorative material.

B. Dental Composites

The disclosed nanoparticles can be incorporated into dental restorative materials. In one embodiment, the nanoparticles are incorporated into dental restorative materials in a concentration of approximately 10% or 30% (depending on the material, be it the adhesive solution, cement, or liner), in order to increase the degree of conversion thereof and the adjacent activated by visible light. The nanoparticles can be incorporated into dental restorative material in a concentration of 10, 11, 12, 13, 14, 15, 16, 17, 18, 19, 20, 21, 22, 23, 24, 25, 26, 27, 28, 29, or 30%.

In one embodiment, the dental restorative material can be an adhesive solution, a liner, dental cement. resin cements, dental ceramics, and composites.

The dental restorative composition can be used as a foundation, base, adhesive, cavity liner, restorative composite resin, or dental resin cement.

III. Methods of Use

The disclosed dental restorative materials having rare earth doped nanoparticles can be used in direct restorative procedures (such as adhesive systems, liners and composite resins) and indirect (resin cements, dental ceramics and composites). It is believed that the disclosed restorative materials have improved properties relative to traditional restorative materials, because of the ability of the nanoparticles to emit light when they are excited by infrared laser. The incorporation of the nanoparticles allows to improve the polymerization of the materials, especially in cavity preparations having great depth, where the light emitted by traditional photoactivating devices cannot reach in an adequate way or in an adequate amount and, thus, to produce high monomeric conversion.

One embodiment provides a method of making dental restorations including steps of applying a dental restoration composition of nanocrystals of rare earth doped $NaYF_4$ having a polyacrylic acid functionalized surface to an affected area of a tooth in a subject in need thereof. Specifically, this nanoparticle-incorporated material is placed on the internal, prepared tooth surfaces, acting as a cavity liner, or a base. In one embodiment, in addition to the nanoparticles, the resin component of the composition contains one or more visible light photoinitiators, conventionally found in such direct photo-curable dental resin compositions. In one embodiment, the initiators require exposure to light in the visible spectral range, specifically within the blue (525 to 490 nm) and/or violet ranges (390 to 425 nm).

After placement in a thin layer, the nanoparticle product (liner, or base) is photocured using a conventional dental visible light curing unit, emitting blue and or blue/violet wavelengths. Subsequent to this exposure and liner/base curing, a conventional dental, photocurable restorative material (commonly referred to as a "composite") can be placed in bulk. Once placed and contoured, the unset material is exposed to the 975 nm laser. Infrared (IR) emission from the laser penetrates the uncured composite paste and strikes the polymerized liner or base material, and will cause the embedded nanoparticles to emit localized visible radiation at the interface between the unpolymerized restorative material and the cured liner/base. In one embodiment, emission of blue and blue/violet emissions from the IR-exposed nanoparticles will result in activation of polymerization near the composite-liner/base interface, causing the composite restorative material to initiate polymerization all along the periphery of the restorative material.

Once this process is completed, the IR-exposed restorative material is then exposed to blue or blue/violet light from the exterior of the restoration using a conventional dental visible photopolymerization unit. In so doing, the bond between the preparation liner or liner/base and the overlying composite restorative material is kept intact. In conventional cases, where no such light is emitted from the preparation periphery, and only visible (blue or blue/violet light) is exposed to the top surface of the bulk-placed composite restorative material, gaps frequently form at the liner or liner/base interface, as a result of polymerization shrinkage of the composite. In one embodiment, the disclosed compositions and methods avoid shrinkage of the composite and allow for more durable, permanent fillings.

In yet another embodiment, the upconverting nanoparticles can be added to a polymerizable dental cement. In such a situation, when cementing a dental ceramic that is translucent to infrared light, exposure of the seated crown to the 975 nm IR laser will result in that radiation energy being transmitted through the ceramic, and directly interacting with the embedded nanoparticles present in the resin cement. The resin cement contains conventional visible light photoinitiators that are sensitive to blue or blueviolet light. Thus, such a nanoparticle incorporated resin cement will generate its own radiant light energy at wavelengths that will activate conventional blue and blue/violet photoinitiators, resulting in the cement polymerizing, and holding the ceramic crown onto the tooth surface.

In one embodiment, the light emitted by the nanoparticles can be blue light at a wavelength near 460 nm or violet light at a wavelength near 400 nm. In one embodiment, the nanocrystals emit light when they are exposed to infrared light, for example at 975 nm.

In one embodiment, the disclosed compositions and methods are for use in dental restorative applications. Subjects in need of such applications can include subjects with tooth decay, dental caries, or tooth erosion. In another embodiment, the disclosed compositions and methods can be used for cosmetic applications such as caps, crowns, and bridges.

EXAMPLES

Example 1: Synthesis of Nanoparticles

Methods
The NPs that were used had a nominal composition of 69.5 mol % of yttrium, 30% of ytterbium and 0.5% of thulium, per mol of sodium. The mass fractions were: 34.0% sodium, 42.8% yttrium, 22.8% ytterbium and 0.4% thulium (dopant compositions: 0-100% ytterbium and 0.1-10% thulium). The nanoparticles were formed by adding trifluoroacetic acid and thulium oxide into a suitable vessel under stirring and controlled temperature and stirring for 20 minutes at room temperature (23° C.). The temperature was then gradually raised using low argon flow due to the volatility of the solution until it reaches 80° C. for the formation of thulium trifluoroacetate. The temperature was maintained at 80° C. for the evaporation of all excess liquid and the solution was cooled to room temperature at 30° C. At this temperature, octadecene and oleic acid were added under agitation and argon flow for 20 minutes. The masses of rare earth elements in the form of $NaCF_3COOH$, $Y(CF_3COOH)_3$ and $Yb(CF_3COOH)_3$ were calculated based on the desired molar ratio. The temperature was raised to 100° C. and held for 30 minutes, then the temperature was raised to 330° C. and held for a further 25 minutes. Finally, the solution was cooled to room temperature.

The synthesis resulted in an organic solution (OS) with particles in suspension. To morphologically evaluate the particles and incorporate them into a dental material, the material was turned into powder form. To do this, the OS was stored in a glass vessel and ethanol (PA) was added, creating a second solution (ES). The ES was centrifuged at 3600 rpm and the supernatant was separated, this operation was repeated 3 times. Then, chloroform was added, creating a solution with the suspended particles (CS). Finally, the mixture was centrifuged for 5 minutes at 12500 rpm (5° C.). The supernatant was removed and excess chloroform was removed by evaporation of the solvent at room temperature, resulting in a white powder of nanoparticles.

For functionalization of the nanoparticles, they were dispersed in a solution of 0.1M HCl and placed in an ultrasonic bath for 1 h in order to remove the oleate binders. The nanoparticles were washed twice with deionized water by centrifugation and re-dispersion. Once extracted, the nanoparticles were dispersed in 15 ml of an aqueous solution (0.5% by weight) at pH 8 of polyacrylic acid (PAA) and kept under vigorous stirring for 1 hour.

The nanoparticle colloid was added to 20 ml of diethylene glycol (DEG) and heated to 100° C. with stirring to evaporate the water content. After approximately two hours, the DEG colloid was placed in an enclosed vial and heated to 130° C. for approximately 17 hours.

The extraction of PAA was performed by centrifugation and re-dispersion in deionized water three times. The success of the functionalization procedure was observed by the formation of a stable aqueous colloid.

In the study on the functionalization of nanoparticles a commercial adhesive solution containing 10% nanoparticles was used.

Example 2: Analysis of Nanoparticles—Tests Performed

Results

The emission spectrum of the nanoparticles was examined using a spectrophotometer. In a dark room, the particles were irradiated with a 975 nm laser and the emission spectrum was captured using suitable software. FIG. 1 shows the spectrum of the nanoparticles when irradiated by the 975 nm laser.

Light emission at wavelengths equivalent to blue light (450 nm and 470 nm), specific for absorption by camphorquinone, as well as at wavelengths capable of activating the shorter wavelength, alternative photoinitiators in some light-activated dental restorative resins in the violet spectral range (400 nm), as well as radiation equivalent to red (800 nm) and green (650 nm) light, may also be observed.

Example 3: X-Ray Dispersive Energy Spectroscopy (EDX)

Methods

To analyze the composition of the nanoparticles, 2 mL of chloroform (PA) was added to the nanoparticle powder, creating a suspension (NS). The NS suspension was applied to the surface of a carbon tape (with the help of a glass rod) on a plastic stub and covered with carbon for evaluation by EDX associated with scanning electron microscopy equipment. The spectrum was obtained using specific software with the following settings: 100 s lifetime, 15 kV, 20-25% dead time and 20 mm working distance.

Results

Figure 2:
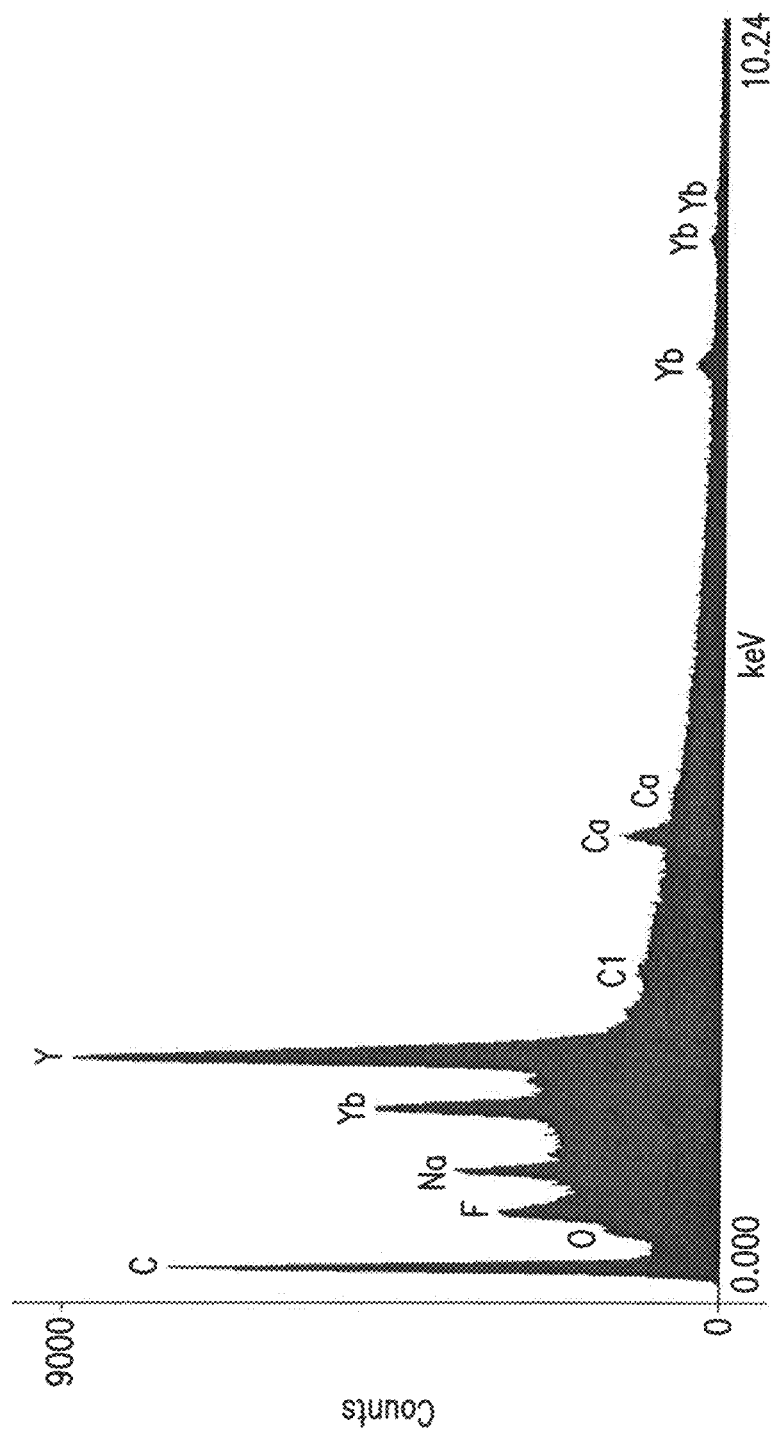
FIG. 2 is a energy dispersive x-ray analysis (EDX) spectral analysis, demonstrating the presence of the elements sodium (Na), yttrium (Y), ytterbium (Yb), chlorine (Cl), calcium (Ca) and fluorine (F) in the synthesized nanoparticles.

FIG. 2 demonstrates the spectrum obtained by EDX analysis. The following chemical elements can be detected: Sodium (Na), Yttrium (Y), Ytterbium, Chlorine (Cl), Calcium (Ca) and Fluorine (F).

Example 4: Scanning Electron Microscopy (SEM)

Methods

The morphology and dispersion of the particles was determined using two different types of microscopy. For SEM analysis, the particles were observed at magnifications of ×10000 and ×20000.

The same NS suspension was placed on a carbon tape on a metal stub and covered with gold at a thickness of approximately 50 Å for analysis in SEM equipment operated with the following parameters: 15 kV, beam width of 25-30 nm and working distance of 10-15 mm.

Results

FIGS. 3A-3B show a suspension with high concentration of nanoparticles, which were not organized in order to configure clusters. The mean particle size was less than 1 μm, confirming the particle size prediction (200 nm).

Example 5: Transmission Electron Microscopy (TEM)

Methods

To determine the shape of the nanoparticles, a suspension containing toluene and nanoparticles was created (TS), in order to obtain a solution of low concentration of nanoparticles, facilitating the observation of their morphology. TS was deposited in specific copper gratings for TEM analysis.

Results

The analysis was performed using the TEM equipment operating at a voltage of 120 kV. The images were obtained at a magnification of ×120,000. It can be seen in FIG. 4 that the nanoparticles had a size of approximately 200 nm and a "disk" (hexagonal structure of the crystals), at a magnification of ×120,000.

Example 6: Analysis of the Incorporated Nanoparticles—Tests Carried Out

Transmission of Light Through Dental Substrates

To determine the percentage of incident light that is transmitted through the different dental substrates, 15 bovine incisors were used, the thickness of the slices of tooth tissues obtained were controlled. The results are seen in Table 1 and FIG. 5.

TABLE 1

Transmission of 975 nm laser light and blue light through different dental substrates.

| Dental substrates | 975 nm (% of incident power) | BL (% of incident power) |
|---|---|---|
| EN1 | 52.9 (±0.4) | 40.9 (±0.9) |
| DE1 | 33.4 (±0.8) | 38.1 (±0.8) |
| DE2 | 15.7 (±0.5) | 14.4 (±0.9) |
| ED2 | 21.9 (±0.2) | 24.4 (±0.4) |
| E1D1 | 25.7 (±0.5) | 26.4 (±0.8) |
| ED2D1 | 16.2 (±0.8) | 15.0 (±1.0) |

In which: EN 1 is enamel with a thickness of 1 mm; DE 1 is 1 mm thick dentin; DE2 is dentin with a thickness of 2 mm; ED2 is enamel-dentin junction with a thickness of 2 mm; E1D1 is enamel with a thickness of 1 mm+1 mm of dentin and ED2D1 is enamel-dentin junction with a thickness of 2 mm+1 mm of dentin.

Transmission of Light (Blue and Infrared) Through Composites

Methods

To determine the percentage of light that is transmitted through dental composites, 6 commercial brands of different composites were selected, the thickness of the specimens being controlled.

Results

Figure 6:
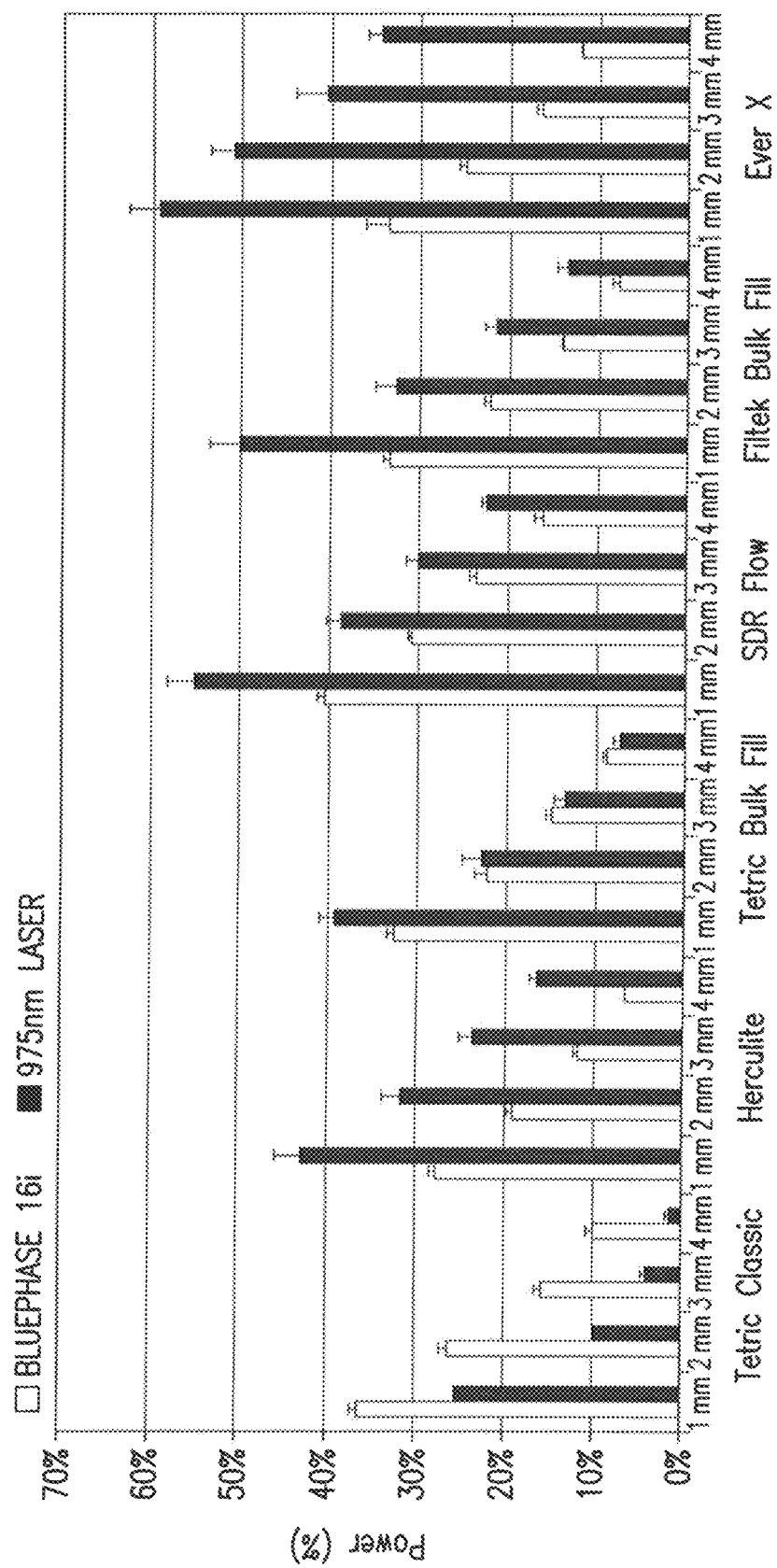
FIG. 6 graphically depicts the transmission of 975 nm laser light as well as of blue light shown different commercial dental composites of varying thicknesses. (Tetric Classic, Ivoclar Vivadent; Herculite, Kerr Dental; Tetric Bulk Fill, Ivoclar Vivadent; SDR Flow, Dentsply/Sirona; Filtek Bulk Fill, 3M/ESPE; EverX, GC Europe).
Figure 7A:
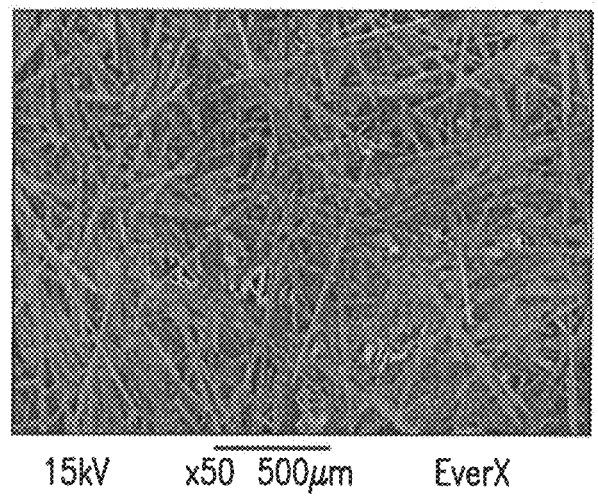
FIG. 7A-7B are micrographs of the inorganic content of a commercial dental resin composite restorative material (EverX, GC Europe) at magnifications of ×50 (FIG. 7A) and ×1,000 (FIG. 7B).
Figure 7B:
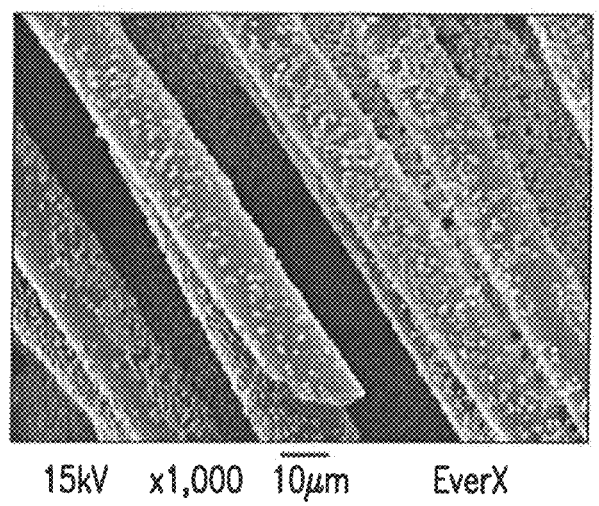

The results can be seen in Table 2 and FIGS. 6 and 7.

TABLE 2

Transmission of 975 nm laser light and blue light through different dental composites in different thicknesses.

| Composite | 975 nm (% of incident power) | BL (% of incident power) |
|---|---|---|
| TETRIC CLASSIC 1 mm | 25.3 (±0.2) | 36.5 (±0.8) |
| TETRIC CLASSIC 2 mm | 9.8 (±0.2) | 26.2 (±1.1) |
| TETRIC CLASSIC 3 mm | 4.1 (±0.3) | 15.7 (±0.7) |
| TETRIC CLASSIC 4 mm | 1.7 (±0.2) | 10.1 (±0.6) |
| HERCULITE 1 mm | 42.9 (±2.8) | 27.9 (±0.4) |
| HERCULITE 2 mm | 31.8 (±2.1) | 19.0 (±0.7) |
| HERCULITE 3 mm | 23.6 (±1.4) | 11.9 (±0.2) |
| HERCULITE 4 mm | 16.4 (±0.9) | 6.3 (±0.2) |
| TETRIC BULK 1 mm | 39.3 (±1.8) | 32.7 (±0.8) |
| TETRIC BULK 2 mm | 22.7 (±2.1) | 22.2 (±1.2) |
| TETRIC BULK 3 mm | 13.4 (±1.2) | 15.0 (±0.4) |
| TETRIC BULK 4 mm | 7.4 (±0.7) | 8.9 (±0.2) |
| SDR FLOW 1 mm | 55.1 (±3.0) | 40.6 (±0.7) |
| SDR FLOW 2 mm | 38.7 (±1-6) | 31.0 (±0.3) |
| SDR FLOW 3 mm | 30.2 (±1.2) | 23.5 (±0.7) |
| SDR FLOW 4 mm | 22.5 (±0.4) | 16.2 (±0.9) |
| FILTEK BULK 1 mm | 50.3 (±3.1) | 33.4 (±0.5) |
| FILTEK BULK 2 mm | 32.8 (±2.5) | 22.2 (±0.6) |
| FILTEK BULK 3 mm | 21.5 (±1.3) | 14.0 (±0.3) |
| FILTEK BULK 4 mm | 13.4 (±1.3) | 7.8 (±0.7) |
| EVERX 1 mm | 59.3 (±3.3) | 33.6 (±2.6) |
| EVERX 2 mm | 51.0 (±2.6) | 25.0 (±0.6) |
| EVERX 3 mm | 40.6 (±3.4) | 16.4 (±0.5) |
| EVERX 4 mm | 34.5 (±1.4) | 11.9 (±0.1) |

Transmission of Light (Blue and Infrared) Through Composites

Methods

To determine the percentage of light that is transmitted through dental ceramics, 6 different types of ceramics were selected, and the thickness of the specimens were controlled.

Results

Figure 8:
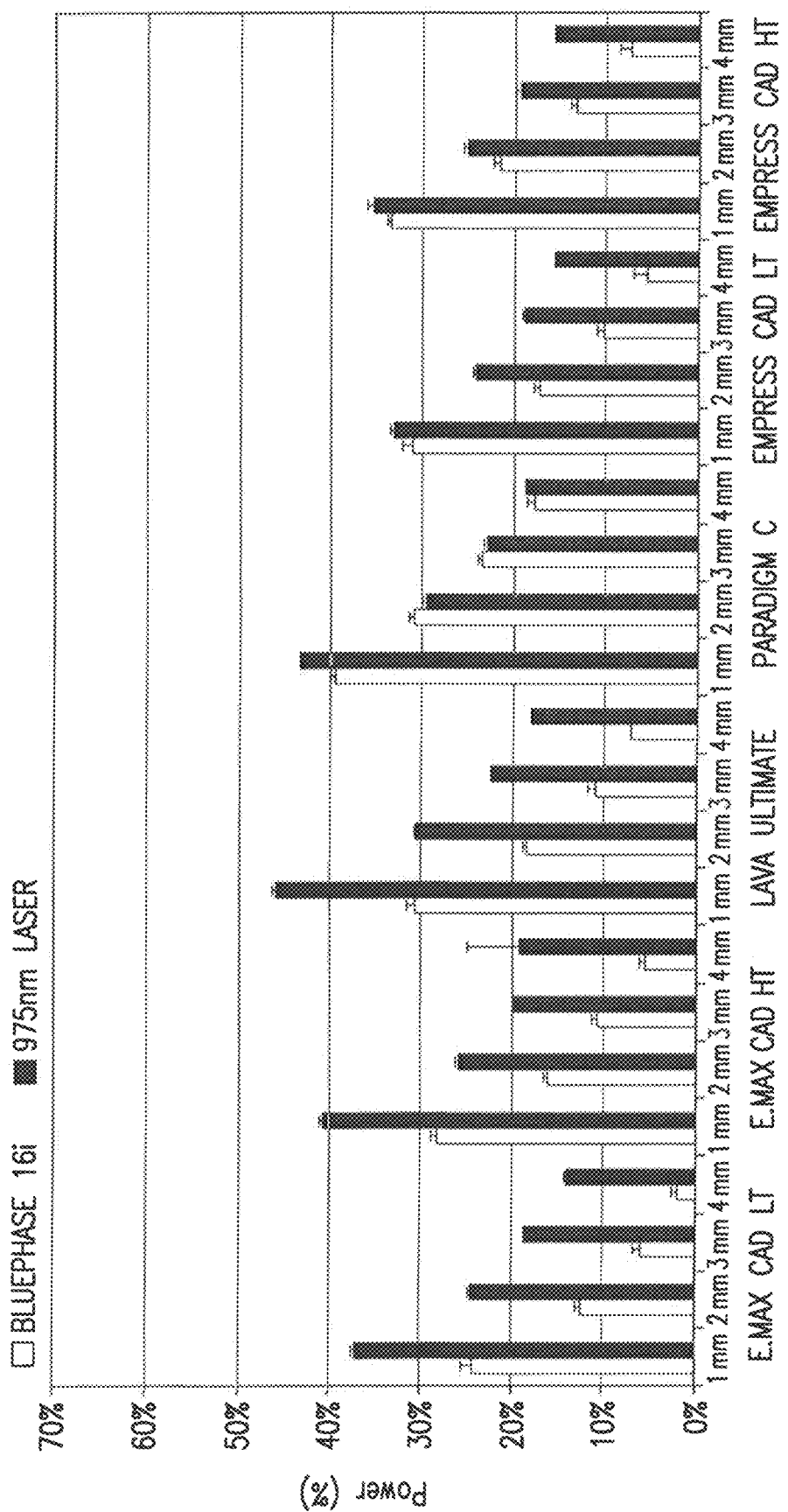
FIG. 8 graphically depicts the transmission of 975 nm laser light and that of a commercial dental, blue LED light (Bluephase 16i, Ivoclar Vivadent) through different commercial dental ceramics of various thicknesses. (E.Max CAD LT, Ivoclar Vivadent; E.Max CAD HT, Ivoclar Vivadent; LAVA Ultimate, 3M/ESPE; Paradigm C, 3M/ESPE; Empress CAD LT, Ivoclar Vavadent; Empress CAD HT, Ivoclar Vavadent)

The results are seen in Table 3 and FIG. 8.

TABLE 3

Transmission of 975 nm laser light and blue light through different dental ceramics in different thicknesses.

| Ceramic | 975 nm (% of incident power) | BL (% of incident power) |
|---|---|---|
| E.MAX LT 1 mm | 37.1 (±0.3) | 24.4 (±1.2) |
| E.MAX LT 2 mm | 24.5 (±0.3) | 12.6 (±0.5) |
| E.MAX LT 3 mm | 18.6 (±0.2) | 6.2 (±0.6 |
| E.MAX LT 4 mm | 14.2 (±0..2) | 2.2 (±0.5) |
| E.MAX HT 1 mm | 40.8 (±0.3) | 28.4 (±0.5) |
| E.MAX HT 2 mm | 25.9 (±0.2) | 16.4 (±0.3) |
| E.MAX HT 3 mm | 20.0 (±0.1) | 10.9 (±0.6) |
| E.MAX HT 4 mm | 19.3 (±5.7) | 5.7 (±0.5) |
| LAVA ULTIMATE 1 mm | 45.9 (±0.4) | 30.9 (±0.9) |
| LAVA ULTIMATE 2 mm | 30.8 (±0.1) | 18.6 (±0.3) |
| LAVA ULTIMATE 3 mm | 22.4 (±0.2) | 11.0 (±0.7) |
| LAVA ULTIMATE 4 mm | 17.9 (±0.1) | 7.2 (±0.1) |
| PARADIGM C 1 mm | 43.2 (±0.2) | 39.6 (±0.4) |
| PARADIGM C 2 mm | 29.6 (±0.4) | 31.0 (±0.4) |
| PARADIGM C 3 mm | 23.0 (±0.3) | 23.6 (±0.3) |
| PARADIGM C 4 mm | 18.6 (±0.1) | 17.8 (±0.7) |
| EMPRESS LT 1 mm | 33.2 (±0.4) | 31.3 (±0.9) |
| EMPRESS LT 2 mm | 24.3 (±0.2) | 17.3 (±0.7) |
| EMPRESS LT 3 mm | 19.0 (±0.2) | 10.3 (±0.6) |
| EMPRESS LT 4 mm | 15.5 (±0.2) | 5.7 (±1.2) |
| EMPRESS HT 1 mm | 35.6 (±0.7) | 33.7 (±0.2) |
| EMPRESS HT 2 mm | 25.3 (±0.2) | 21.6 (±0.5) |
| EMPRESS HT 3 mm | 19.4 (±0.5) | 13.4 (±0.5) |
| EMPRESS HT 4 mm | 15.5 (±0.2) | 7.5 (±1.0) |

Emission Spectrum Analysis

Methods

In order to determine the blue light emission spectrum generated by the resin discs at different concentrations (15%, 30% and 60%) and how much blue light is converted through the amount of infrared remaining after passing through a substrate, a calibrated configuration for spectrophotometric analysis and the 975 nm infrared laser was positioned at 100 mm from the resin disk, perpendicular to the surface thereof.

Results

Figure 9:
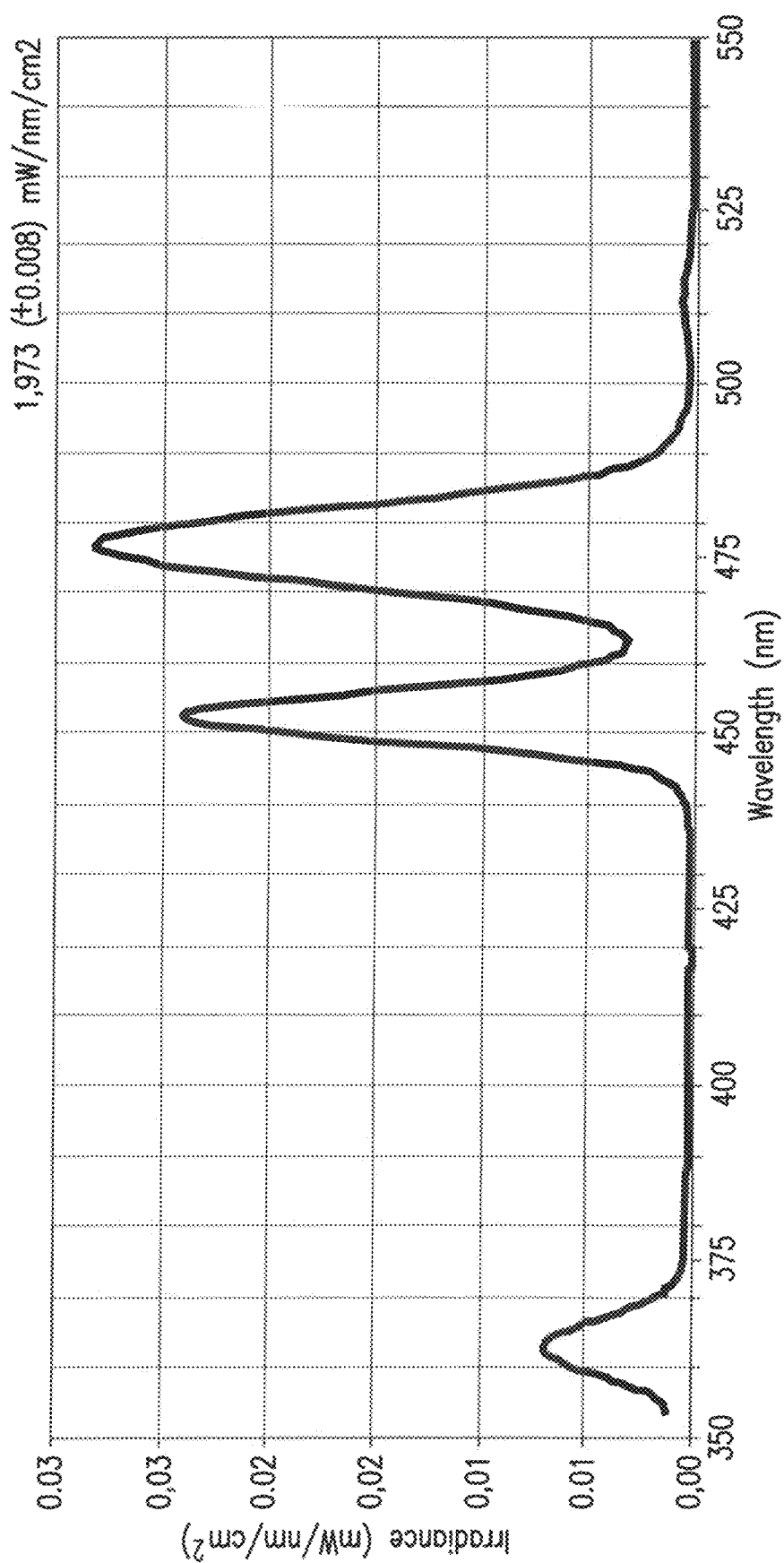
FIG. 9 shows the visible light spectrum emitted from a disc fabricated from a polymerized dental bonding agent (Heliobond, Ivoclar/Vivadent) seeded with 30% nanoparticles, and exposed to the 975 nm laser.
Figure 10A:
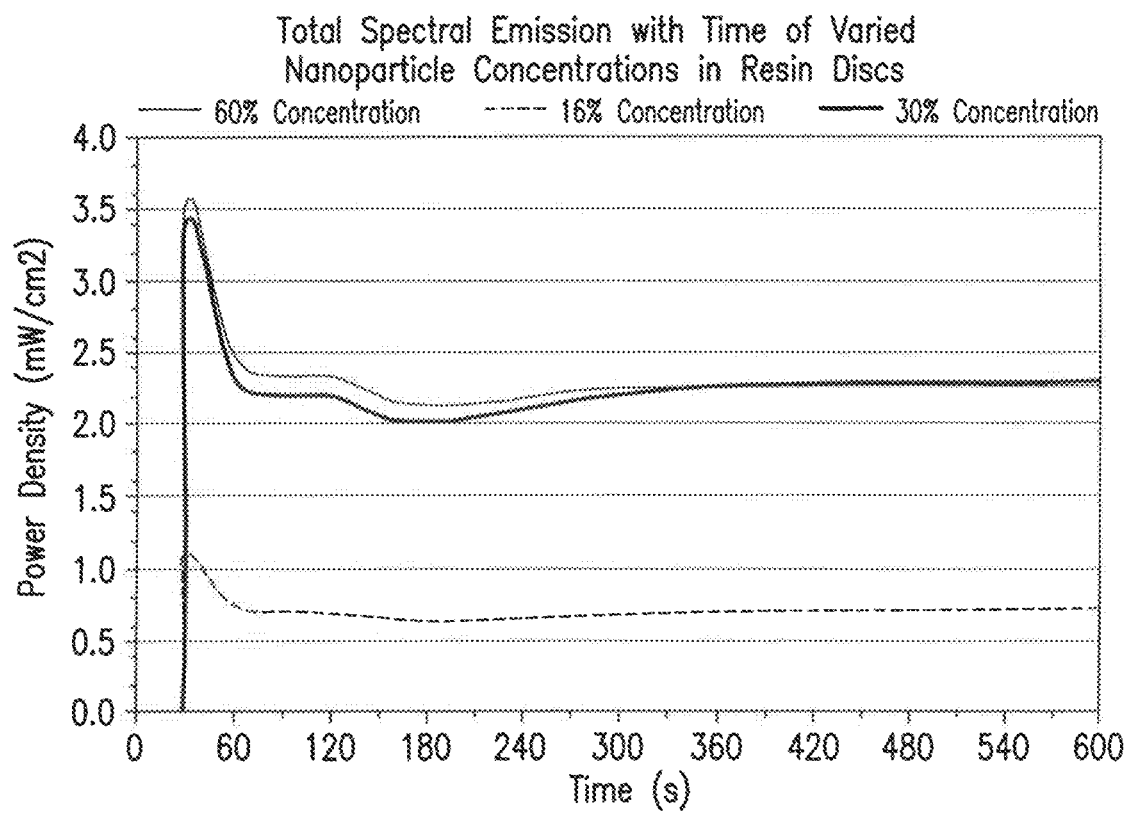
FIGS. 10A-10D show the visible light emission using the upconversion effect of the nanoparticles on IR laser-exposed resin discs of a commercial dental bonding agent (Heliobond, Ivoclar/Vivadent), seeded with different nanoparticle concentrations, with respect to IR exposure time.
Figure 10B:
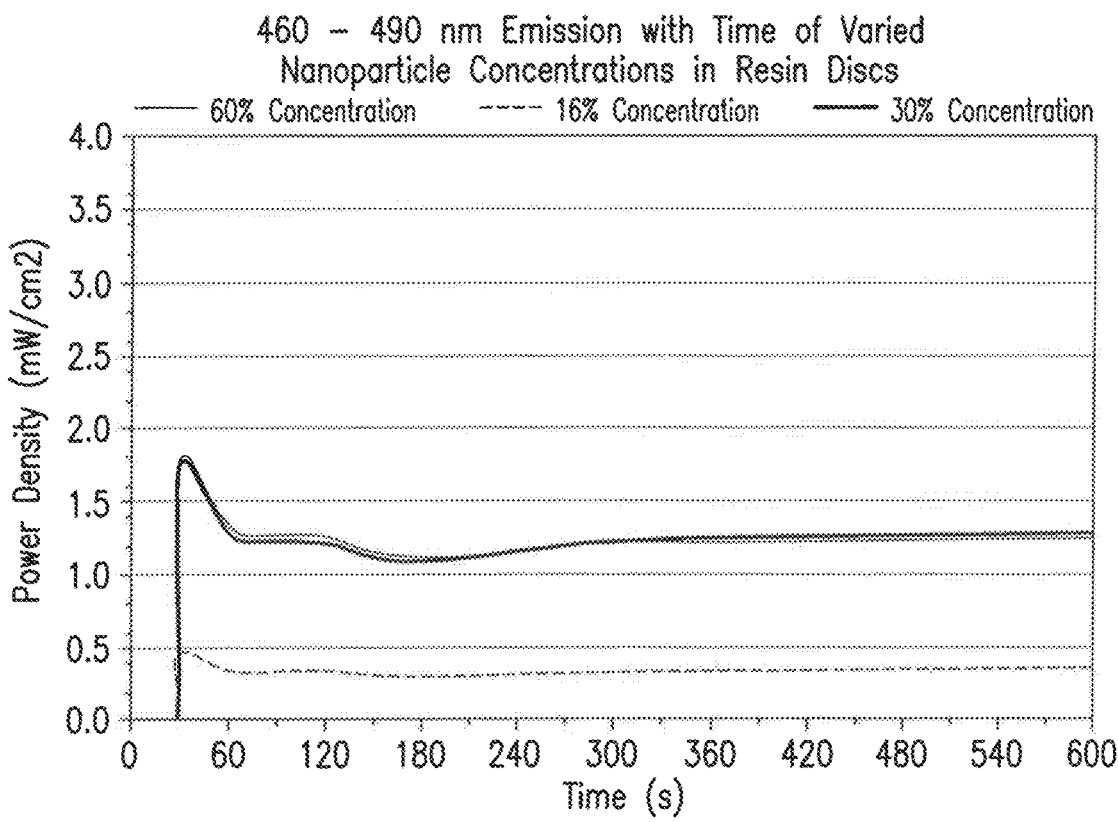
Figure 10C:
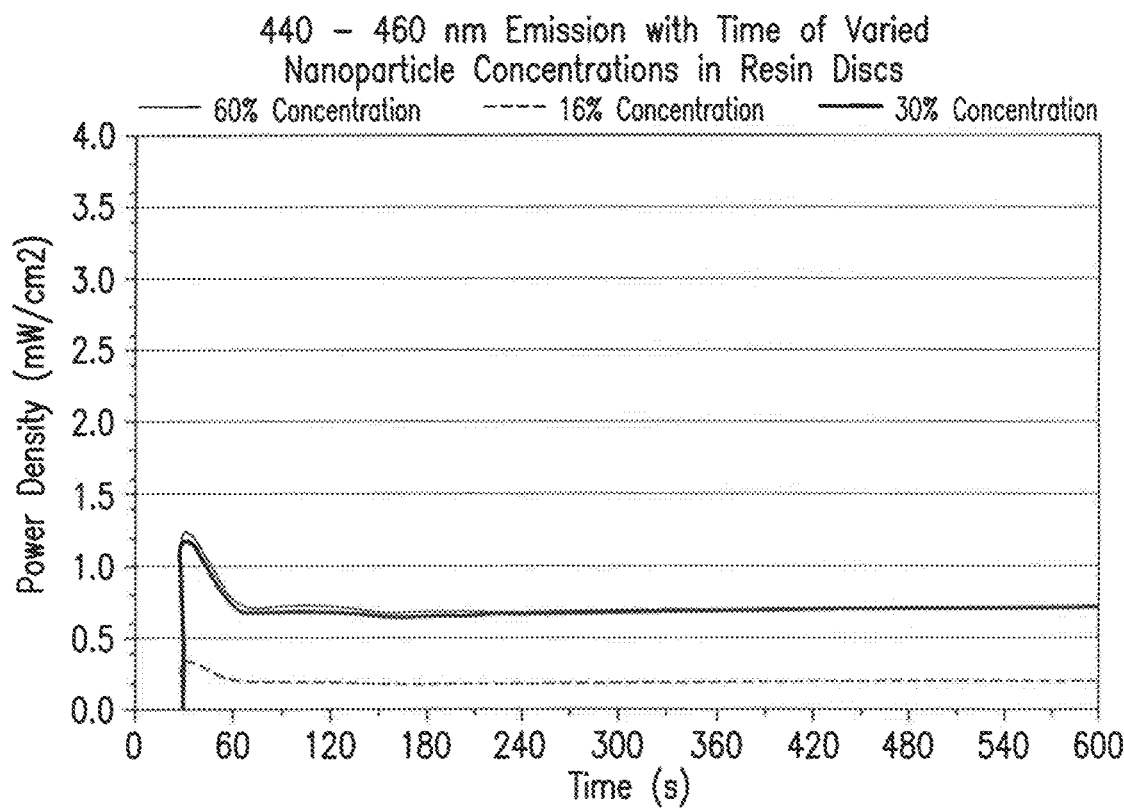
Figure 10D:
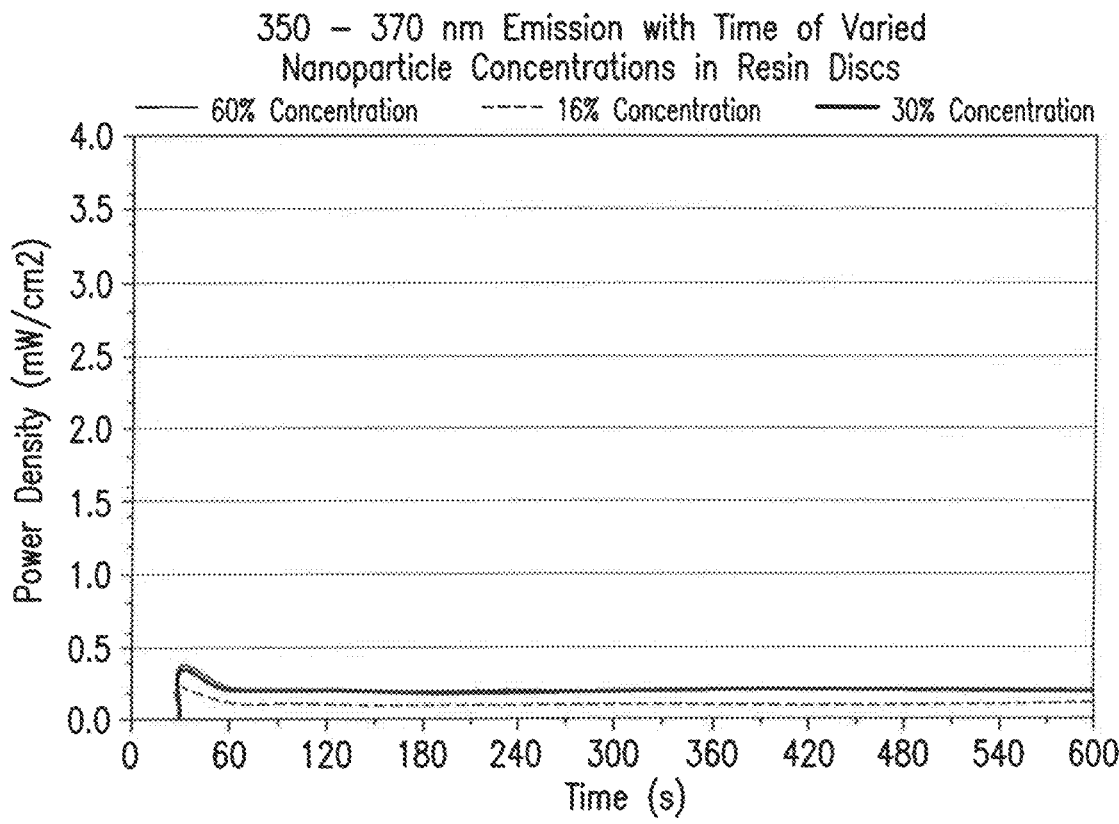

Light emission from resin disks showed peaks in the regions of 450 nm (blue), 475 nm (blue) and 365 nm (violet). This latter peak can be of extreme importance for use with resins that use alternative photoinitiators, of greater efficiency (FIG. 9).

The different concentrations (15%, 30% and 60%) were compared according to the exposure time. Thus, it was possible to determine which concentration would present the greatest efficiency from the upconversion effect, and, consequently, be used for the subsequent methodologies.

In addition, the emission of each specific wavelength was evaluated over a 600-s long exposure (FIG. 10). According to the results, it was possible to determine that the nanoparticle concentration of 30% as the most suitable for use.

Figure 11:
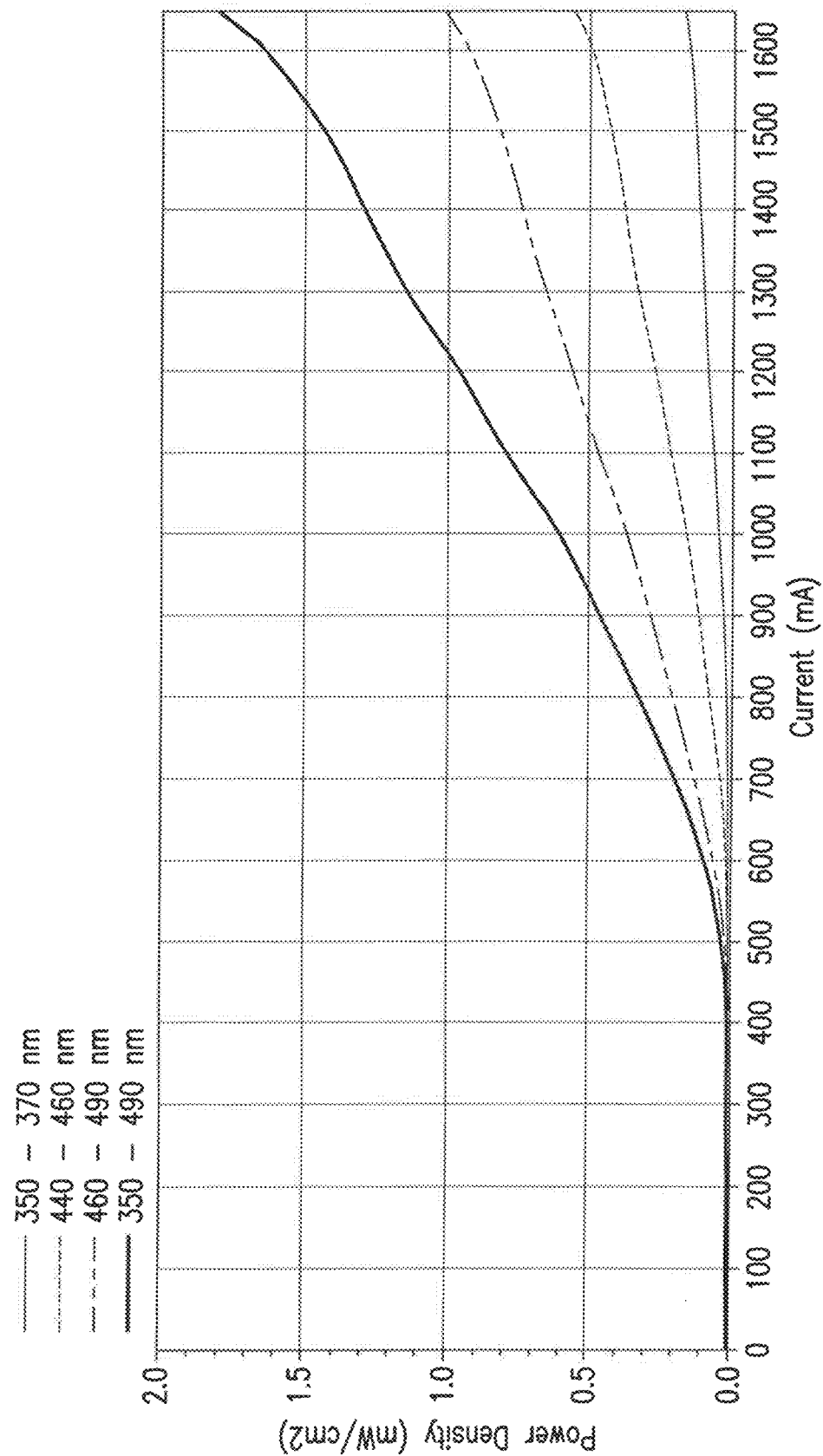
FIG. 11 shows the conversion efficiency of infrared light into blue light by the polymerized disc of commercial dentin bonding agent (Heliobond, Ivoclar/Vivadent) seeded with 30% nanoparticles, with respect to the amount of current (mA) supplied to the IR laser diode.

The efficiency of infrared conversion in blue by the resin disc containing the nanoparticles was also evaluated. The laser current controller was increased from 100 to 1600 mA and the power density emission of the resin disc was evaluated (FIG. 11).

Figure 12:
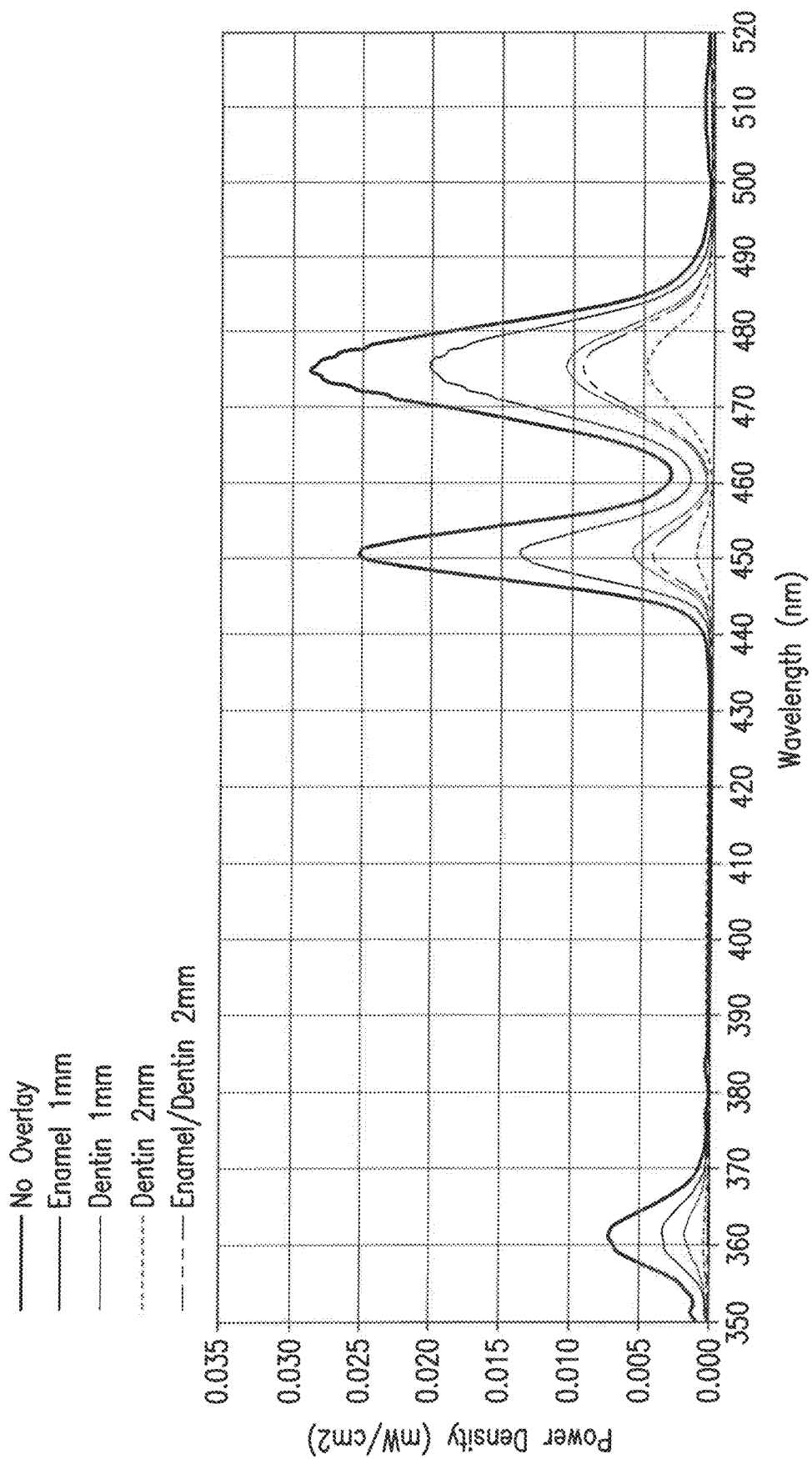
FIG. 12 presents the visible light emission spectrum resulting from infrared exposure of a polymerized disc of commercial dental resin adhesive bonding agent (Heliobond, Ivoclar/Vivadent) seeded with the nanoparticles, after the IR radiation has passed through various thicknesses of tooth tissues.
Figure 13:
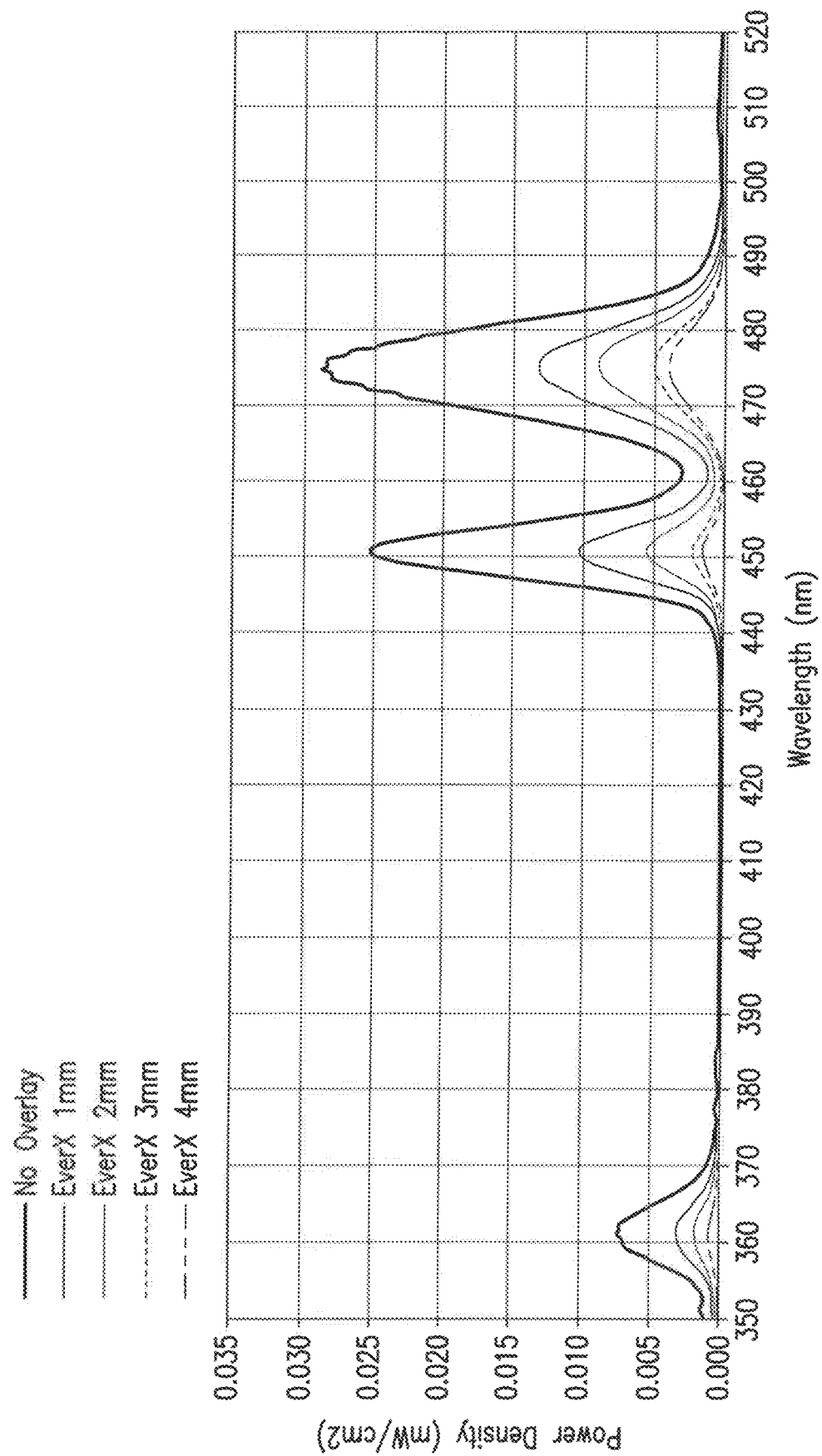
FIG. 13 presents the visible light emission spectrum resulting from infrared exposure of a polymerized disc of a commercial dental resin adhesive bonding agent (Heliobond, Ivoclar/Vivadent) that was seeded with the nanoparticles, after the IR radiation has passed through various thicknesses of a commercial composite restorative material, EverX (GC Corporation).
Figure 14:
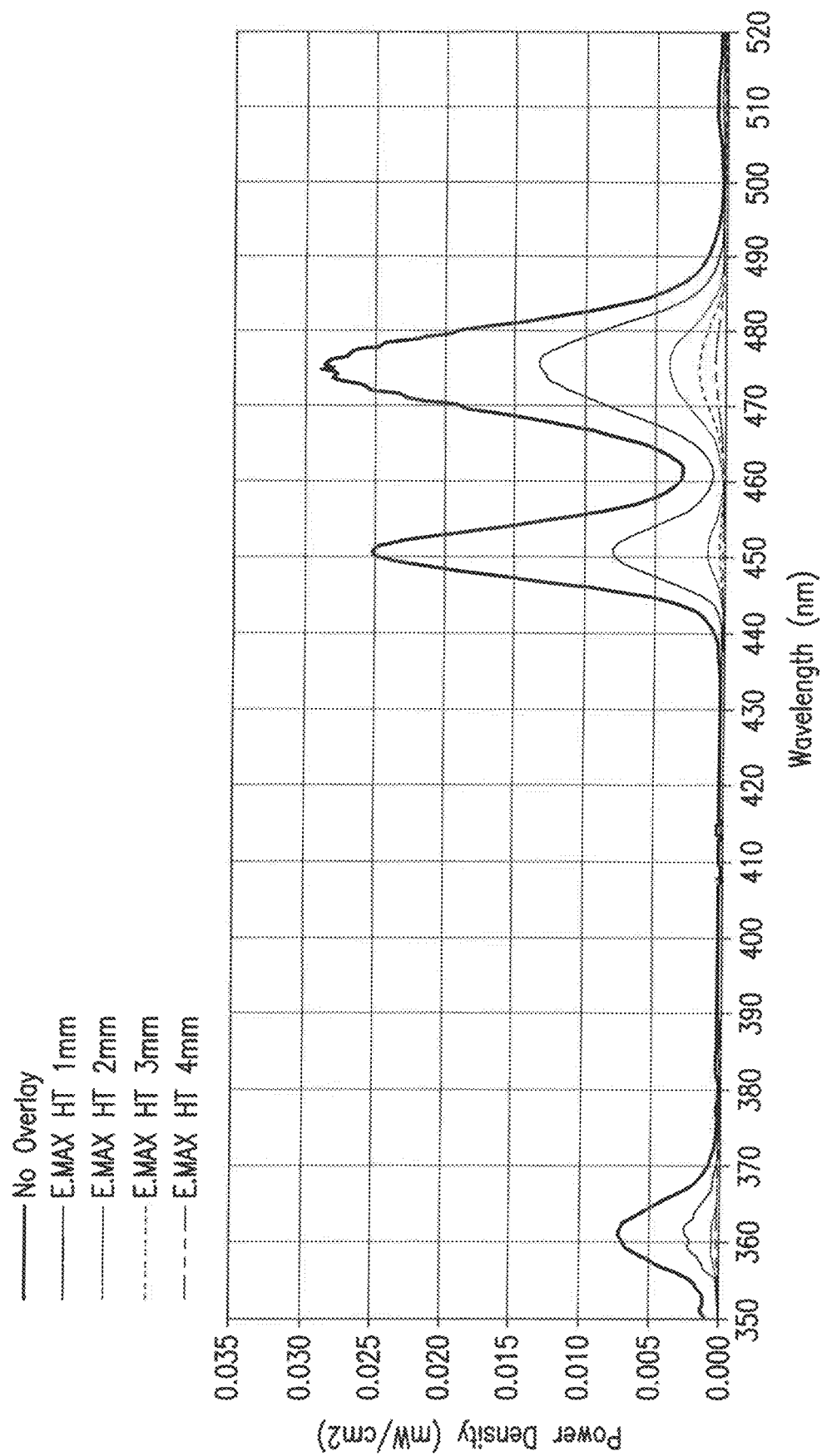
FIG. 14 presents the visible light emission spectrum after infrared exposure of a commercial dental resin adhesive bonding agent seeded with the nanoparticles (Heliobond, Ivoclar/Vivadent) after the IR radiation has passed through various thicknesses of a commercial dental ceramic material (E.MAX HT, Ivoclar Vivadent).

Thereafter, the conversion of light was evaluated when a substrate was interposed between the light source and the resin disk. This analysis evaluated the interposition of different dental substrates (FIG. 12), dental composites in different thicknesses (FIG. 13), and dental ceramics in different thicknesses (FIG. 14).

Fourier Transform Infrared Spectroscopy (FTIR)

Methods

To evaluate the effect of blue light on the cure of a pure resin, Fourier transform infrared spectroscopy (FTIR) methodology was used.

To determine the degree of conversion (%) promoted by the nanoparticles in a pure resin under dental substrates, samples similar to those used for the light transmission test were used.

Results

Figure 15:
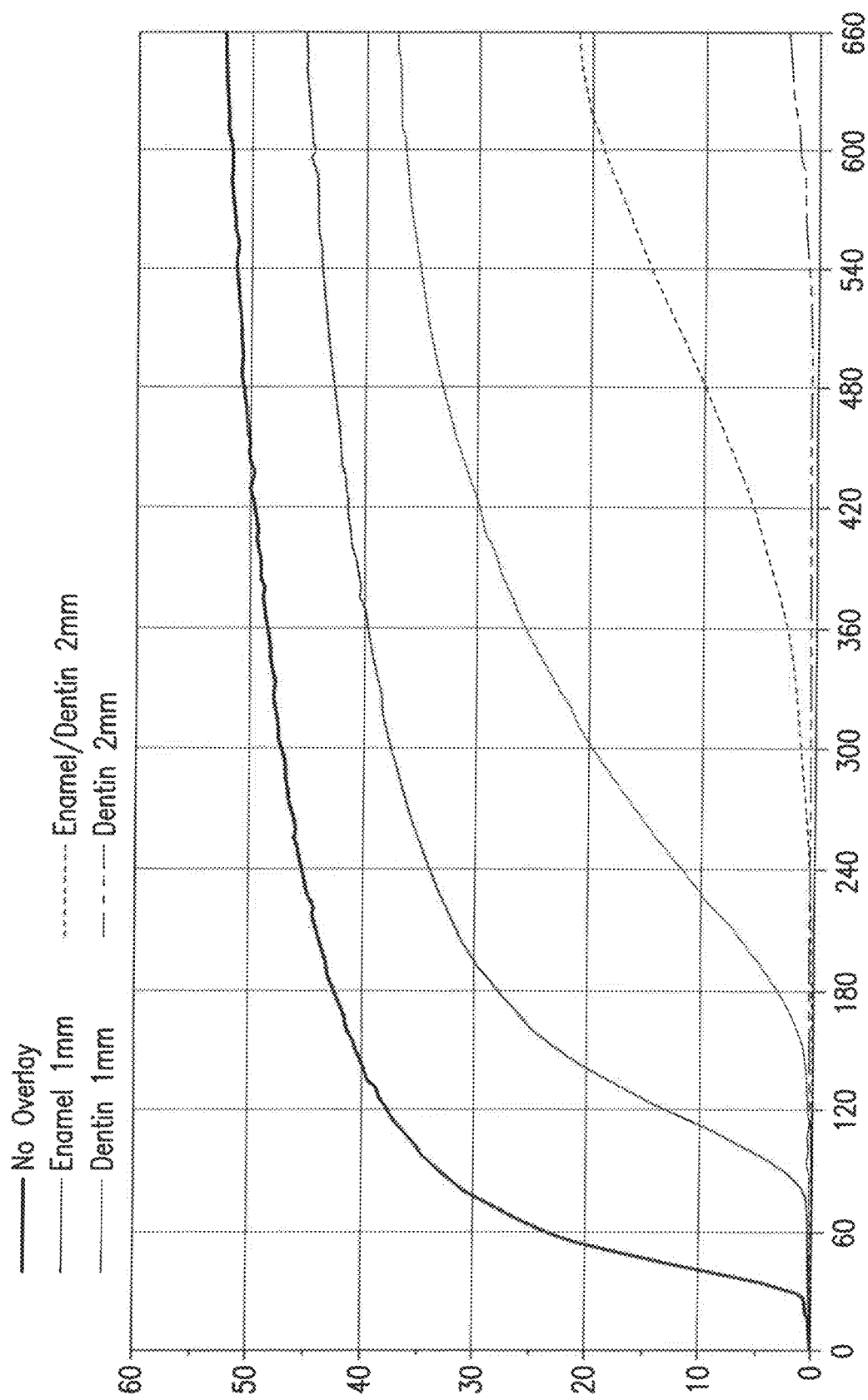
FIG. 15 graphically depicts the time-based curing profile (Y-axis representing % monomer conversion) of a commercial dental resin adhesive bonding agent seeded with the nanoparticles (Heliobond, Ivoclar/Vivadent) when the 975 nm laser was shined through various thicknesses and types of tooth tissues.
Figure 16:
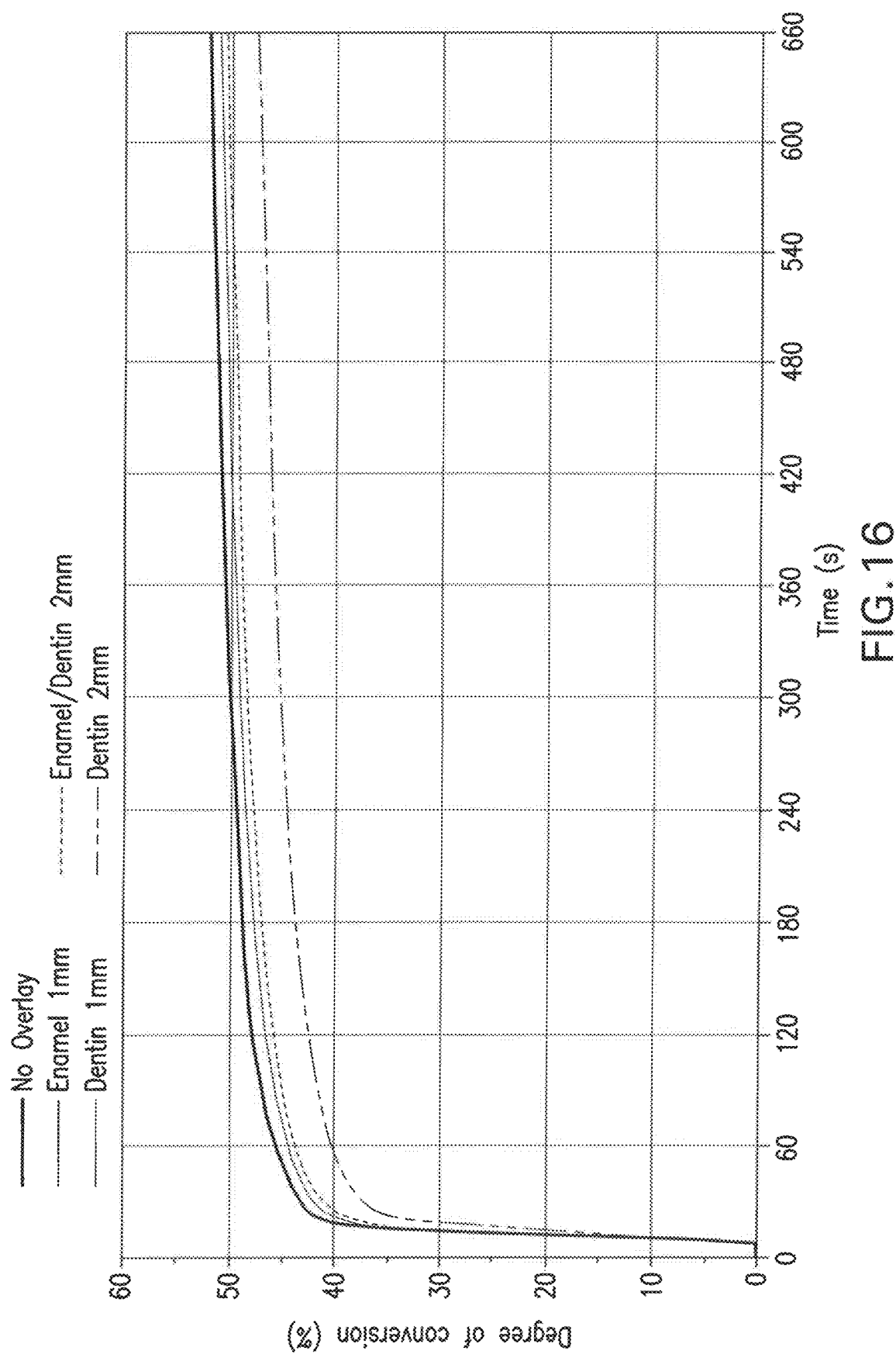
FIG. 16 graphically depicts the time-based curing profile of a commercial dental resin adhesive bonding agent seeded with the nanoparticles (Heliobond, Ivoclar/Vivadent) using a commercial, blue, LED-based dental light curing unit (Bluephase 16i, Ivoclar/Vivadent), that was shined through various thicknesses and types of tooth tissues.

Thus, 15 bovine incisors were used and eight groups were analyzed for this assay (n=5). The results are shown in Table 4 below and FIGS. 15 and 16.

TABLE 4

Monomer conversion (%) of Heliobond to 975 nm exposure of 300 or 600 s using different activation protocols under different dental substrates.

| Group | Monomer Conversion (%) | |
|---|---|---|
| | 300 s | 600 s |
| BLHBEN | 50.0 (±0.5) | 51.8 (±0.4) |
| BLHBDE1 | 49.3 (±0.5) | 50.9 (±0.5) |
| BLHBDE2 | 45.3 (±1.3) | 47.4 (±1.1) |
| BLHBED | 48.6 (±1.9) | 50.4 (±1.7) |
| 975NPEN | 37.6 (±1.6) | 44.7 (±1.2) |
| 975NPDE1 | 24.1 (±8.1) | 38.8 (±2.0) |
| 975NPDE2 | 0.4 (±0.3) | 1.8 (±1.3) |
| 975NPED | 1.4 (±1.7) | 19.1 (±5.8) |

In which: BLHBEN is blue light through 1 mm-thick enamel; BLHBDE1 is blue light through 1 mm-thick dentin; BLHBDE2 is blue light through 2 mm-thick dentin: BLHBED is blue light through the enamel-dentin junction with 2 mm thickness; 975NPEN is 975 nm infrared laser through 1 mm-thick enamel; 975NPDE1 is 975 nm infrared laser through 1 mm-thick dentin; (975NPDE2) is 975 nm infrared laser through 2 m-thick dentin, and 975NPED is 975 nm infrared laser through the enamel-dentin junction with 2 mm thickness.

Interposition of Different Composites in Different Thicknesses

Methods

To determine the degree of conversion (%) promoted by the nanoparticles in a pure resin under a dental composite, samples similar to those used for the light transmission test were used.

To this end, a commercial dental composite (EverX, GC Europe) was selected for the test, because of its increased light transmission within the infrared wavelength.

Results

Figure 17:
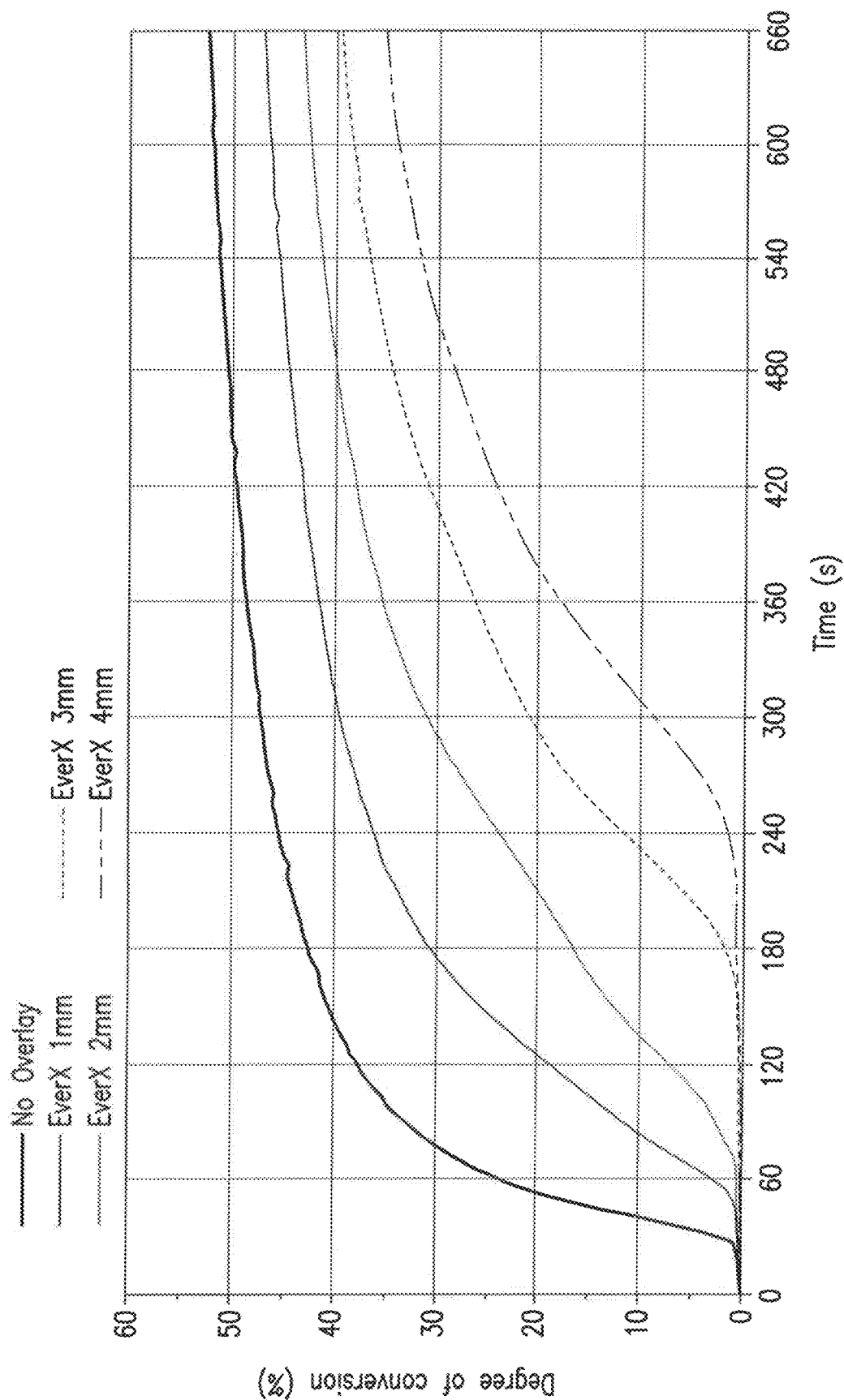
FIG. 17 graphically depicts the time-based curing profile of a commercial dental resin adhesive bonding agent seeded with the nanoparticles (Heliobond, Ivoclar/Vivadent), when exposed to a 975 nm that was filtered first through various thicknesses of a commercial dental resin composite (EverX, GC Europe).
Figure 18:
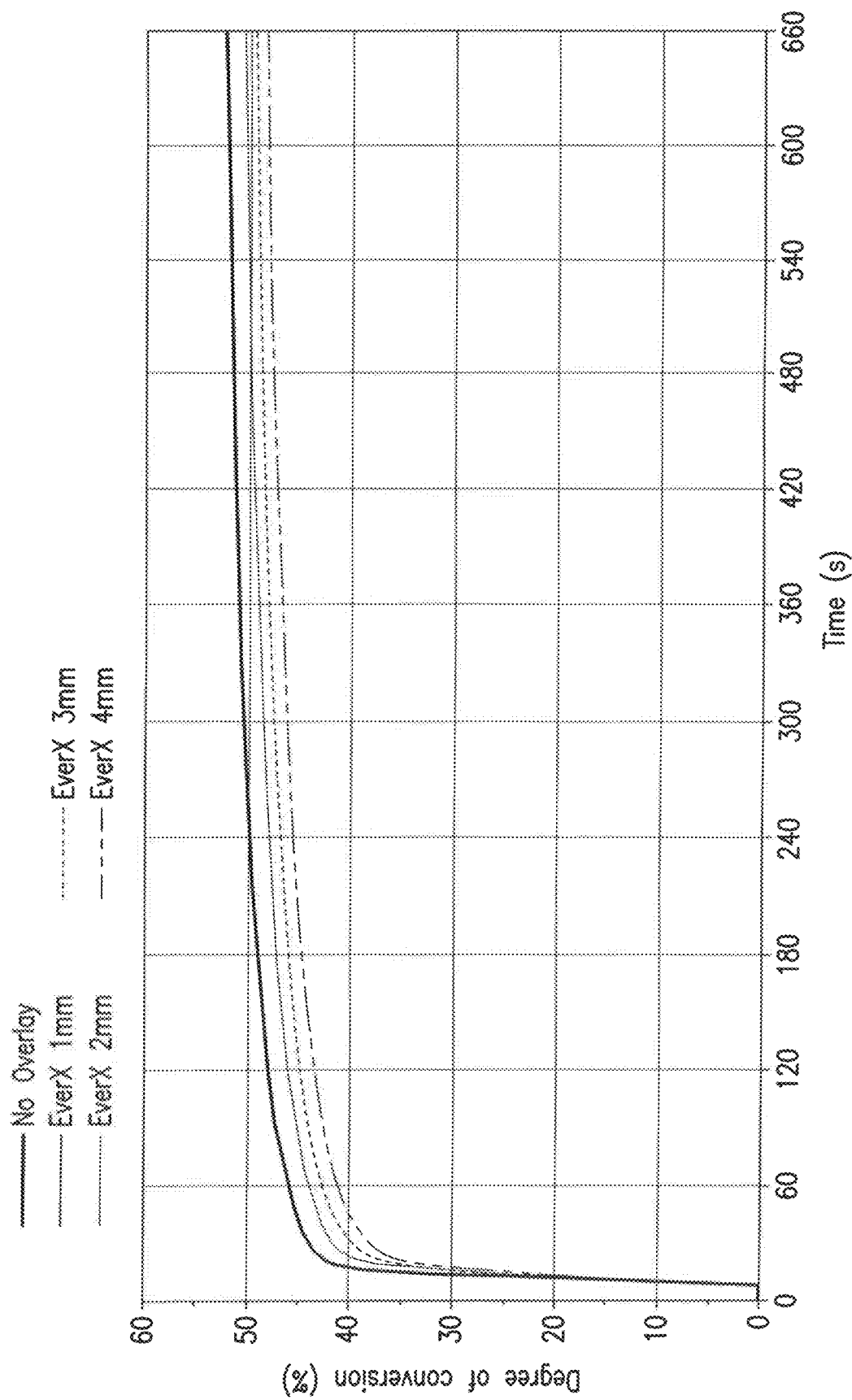
FIG. 18 graphically depicts the time-based curing profile of a commercial dental resin adhesive agent (Heliobond, Ivoclar/Vivadent) that was exposed to a commercial, blue, LED-based dental light curing source (Bluephase 16i, Ivoclar/Vivadent), when sined through various thicknesses of a commercial dental composite restorative material (EverX, GC Europe).
Figure 19A:
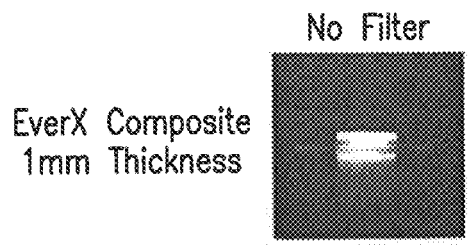
FIGS. 19A-19P are images obtained using a digital camera through filters specific to each wavelength of blue light, capturing the upconversion effect of a resin disc containing nanoparticles having optical fluorescence properties.
Figure 19B:
Figure 19C:
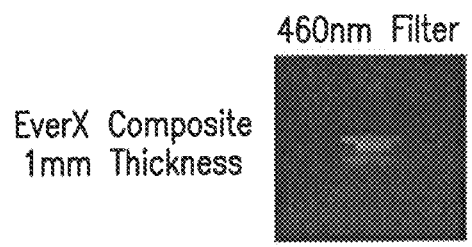
Figure 19D:
Figure 19E:
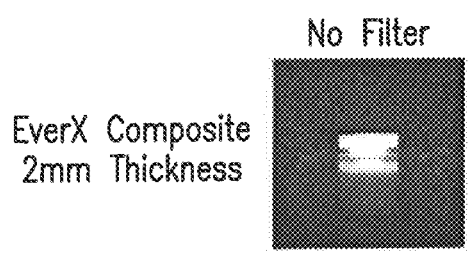
FIGS. 19E-19H show the same effect, but through 2 mm thickness of the same commercial composite.
Figure 19F:
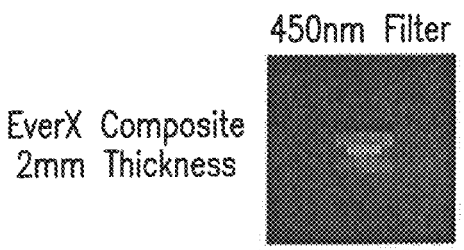
Figure 19G:
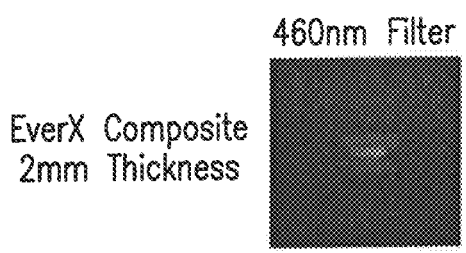
Figure 19H:
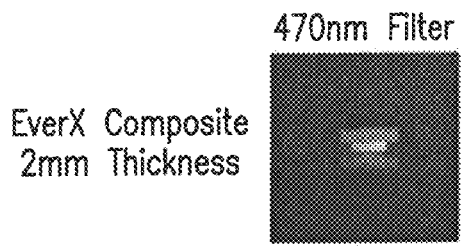
Figure 19I:
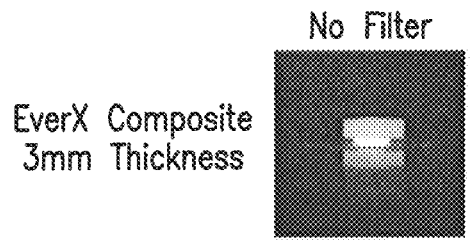
FIGS. 19I-19L show the results using 3 mm thickness of this composite.
Figure 19J:
Figure 19K:
Figure 19L:
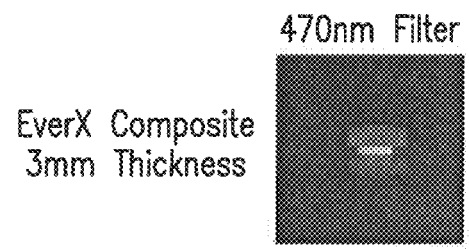
Figure 19M:
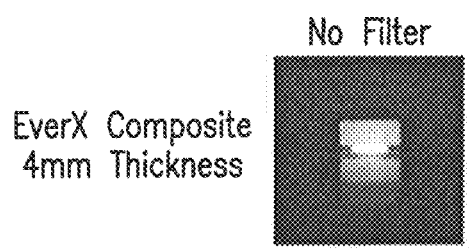
Figure 19N:
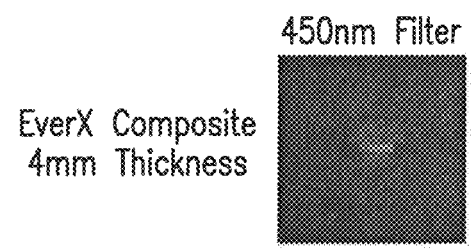
Figure 19O:
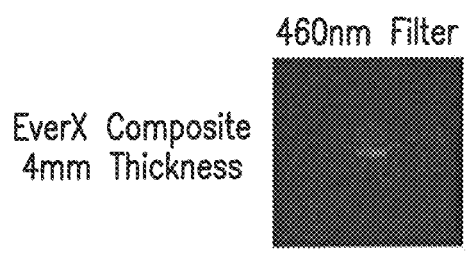
Figure 19P:
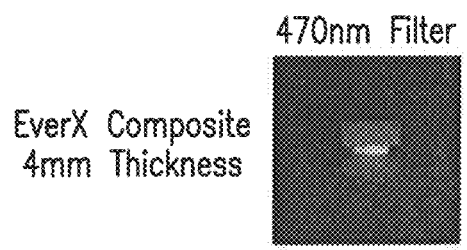

Eight groups were analyzed (n=5) and the results are shown in Table 5 below and FIGS. 17, 18, and 19.

TABLE 5

Degree of conversion (%) of Heliobond to 300 s and 600 s using different protocols of activation under EverX dental composite in different thicknesses.

| Group | Monomer Conversion (%) | |
|---|---|---|
| | 300 s | 600 s |
| BLHBEX1 | 50.6 (±0.4) | 52.2 (±0.4) |
| BLHBEX2 | 48.6 (±1.0) | 50.5 (±1.1) |
| BLHBEX3 | 47.4 (±1.6) | 49.4 (±1.5) |
| BLHBEX4 | 46.4 (±1.4) | 48.3 (±1.6) |

TABLE 5-continued

Degree of conversion (%) of Heliobond to 300 s and 600 s using different protocols of activation under EverX dental composite in different thicknesses.

| Group | Monomer Conversion (%) | |
|---|---|---|
| | 300 s | 600 s |
| 975NPEX1 | 39.3 (±4.3) | 46.2 (±2.6) |
| 975NPEX2 | 34.4 (±6.3) | 43.7 (±2.8) |
| 975NPEX3 | 26.1 (±3.6) | 40.4 (±1.2) |
| 975NPEX4 | 8.5 (±5.8) | 33.8 (±4.9) |

In which: BLHBEX1 is blue light shown through 1 mm thickness of EverX; BLHBEX2 is blue light shown through 2 mm thickness of EverX; BLHBEX3 is blue light shown through 3 mm thickness of EverX; BLHBEX4 is blue light shown through 4 mm thickness of EverX; and 975NPEX1 is 975 nm infrared laser shown through 1 mm thickness of EverX; 975NPEX2 is 975 nm infrared laser shown through 2 mm thickness of EverX; 975NPEX3 is 975 nm infrared laser show through 3 mm thickness of EverX, and 975NPEX4 is 975 nm infrared laser shown through 4 mm thickness of EverX.

Post-Infrared Blue Light Activation

Methods

In order to analyze the influence of an initial 10-minute exposure from a 975 nm laser on the final degree of monomer conversion (%) of a bluelight photocurable, commercial, dental adhesive resin (Heliobond, Ivoclar/Vivadent) which was seeded with the nanoparticles, an additional 10-second exposure to the commercial blue, LED dental curing light (Bluephase 16i, Ivoclar/Vivadent) was made on the same specimens previously exposed to only the laser.

Results

Figure 20:
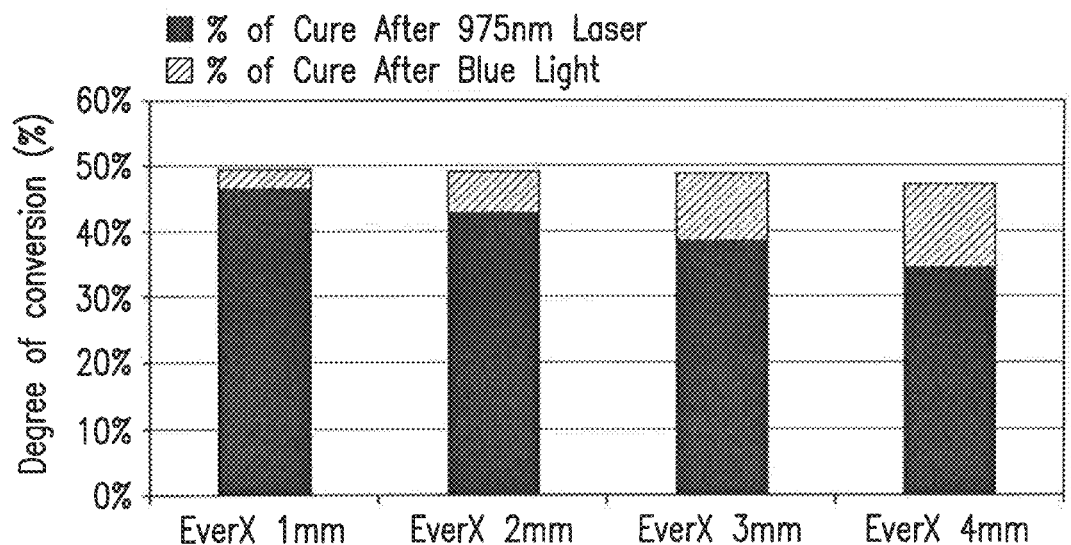
FIG. 20 graphically depicts the degree of conversion (%) of a blue-light, photocurable, commercial dental resin-based bonding agent (Heliobond, Ivoclar/Vivadent) that was seeded with the nanoparticles, after a 10-minute long exposure to a 975 nm laser, as well as then the material was directly exposed to a 10-second long blue, LED, commercial dental light curing unit (Bluephase 16i, Ivoclar/Vivadent).

Four experimental groups were evaluated (n=5) and the results are shown in Table 6 and FIG. 20.

TABLE 6

Monomer conversion (%) of Heliobond seeded with nanoparticles to an initial 600 s exposure to the 975 nm laser and a subsequent 10 s exposure to a commercial blue LED-based dental light curing unit (Bluephase 16i, Ivoclar/Vivadent) that was placed underneath discs of a commercial dental composite (EverX, GC Europe) of different thicknesses.

| Group | Conversion Rate (%) | |
|---|---|---|
| | 600 sec (laser 975 nm) | 10 sec (blue light) |
| B9NPEX1 | 46.18 (±2.62) | 49.42 (±2.62) |
| B9NPEX2 | 43.67 (±2.78) | 49.01 (±) |
| B9NPEX3 | 40.38 (±1.20) | 48.73 (±) |
| B9NPEX4 | 33.82 (±4.85) | 47.13 (±) |

In which: B9NPEX1 is 10 s exposure of blue light after an initial 10 min exposure to the infrared laser at 975 nm for through 1-mm thickness of a commercial dental adhesive resin (EverX, GC Europe); B9NPEX2 is 10 s exposure of blue light after an initial 10 min exposure to the infrared laser at 975 nm through 2-mm thickness of a commercial dental adhesive resin (EverX, GC Europe); B9NPEX3 is 10 s exposure of blue light after an initial 10 min exposure to the infrared laser at 975 nm through 3-mm thickness of a commercial dental adhesive resin (EverX, GC Europe); and B9NPEX4 is 10 s exposure of blue light after an initial 10 min exposure to the infrared laser at 975 nm through 4-mm thickness of a commercial dental adhesive resin (EverX, GC Europe).

Example 7: Functionalized Nanoparticles Analysis—Tests Performed

Transmission Electron Microscopy (TEM)
Methods

Samples of an unpolymerized commercial dental adhesive resin material (Heliobond, Ivoclar/Vivadent) containing functionalized or non-functionalized nanoparticles (control) were prepared. Both samples were placed under a jet of air for 1 minute to evaporate the remaining chloroform prior to photoactivation.

The resins were placed in silicone molds and photoactivated for 20 s using a commercial blue, LED-based dental light curing unit (Bluephase 16i, Ivoclar/Vivadent) to obtain a solid disc of each resin. Ultrafine portions of the polymerized materials were collected on screens of 200 copper networks and observed using transmission electron microscopy operated at 80 kV.

Results

Figure 21:
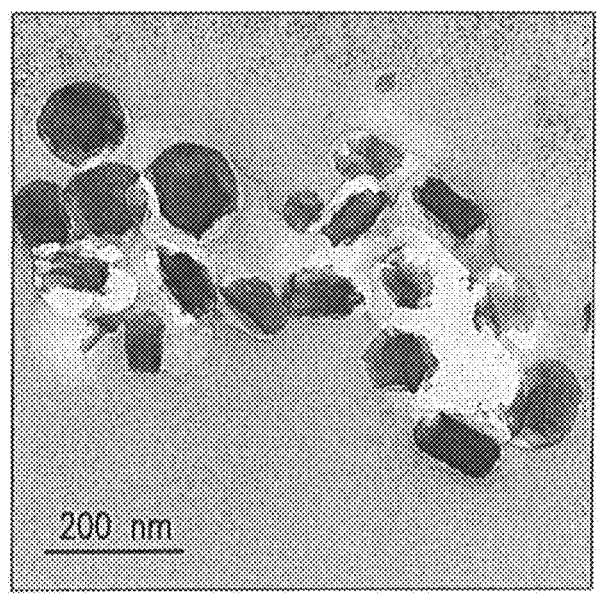
FIG. 21 shows a TEM image of non-functionalized nanoparticles incorporated into the polymerized, commercial dental adhesive resin (Heliobond, Ivoclar/Vivadent). Because of the non-functionalization, these particles are not intimately attached to the resin matrix of the dental adhesive, and gaps are present.
Figure 22:
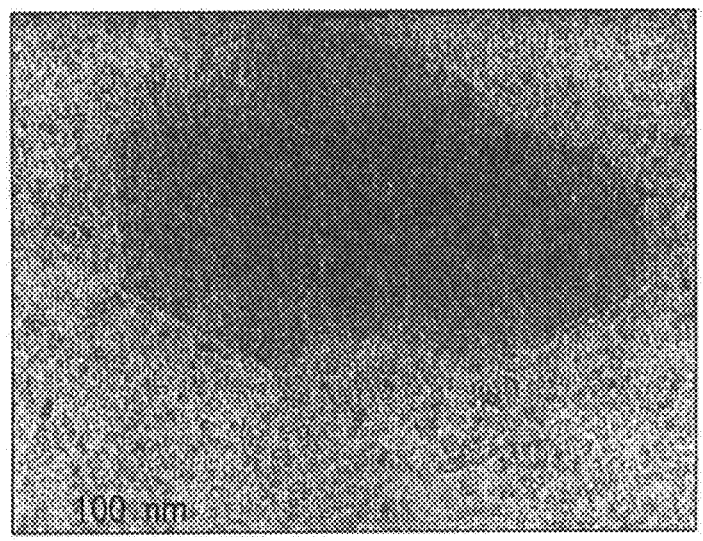
FIG. 22 shows a TEM image of a functionalized nanoparticle incorporated into the polymerized, commercial dental adhesive resin (Heliobond, Ivoclar/Vivadent). Because of the functionalized coating of the particle, the three hexagonal nanoparticles are chemically bound to the resin matrix of the dental adhesive, demonstrating an intimate interfacial wetting/bonding of the functionalized particles and the polymerizable resin matrix.

FIG. 21 shows images of non-functionalized nanoparticles added to the adhesive, while FIG. 22 presents images of the functionalized particles embedded within and chemically bonded to the polymerized dental adhesive resin surrounding them. Because of the intimate adaptation of the resin matrix to the boundaries of the functionalized nanoparticles, this suggests strong evidence that the functionalization of the UCNP was effective positive.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A dental liner composition comprising:
   nanoparticles comprising nanocrystals of NaYF4 doped with 69.5% mole of yttrium, 30% mole of ytterbium, and 0.5% mole of thulium, per mole of sodium, wherein the surface of the nanoparticles is functionalized with polyacrylic acid.

2. The dental liner composition of claim 1, wherein the nanoparticles comprise 10%-30% of the composition.

3. The dental liner composition of claim 1, wherein the nanocrystals are hexagonal shaped.

4. The dental liner composition of claim 1, wherein the nanocrystals have a particle size ranging from 100 to 200 nm.

5. A method of making direct dental restorations in a subject in need thereof, comprising:
   applying the dental liner composition of claim 1 to a prepared surface area of a tooth;
   curing the dental liner composition using a visible light curing unit that emits blue and or blue/violet wavelengths;
   placing a direct dental, photocurable restorative material over the cured dental liner composition and optionally contouring the direct dental, photocurable restorative material; and
   curing the direct dental, photocurable restorative material with infrared light,
   wherein the infrared light penetrates the uncured direct dental, photocurable restorative material and strikes the cured dental liner composition causing the nanoparticles in the cured dental liner composition to emit localized visible radiation at the interface between the unpolymerized direct dental, photocurable restorative material and the cured dental liner composition, wherein the visible radiation initiates polymerization of the direct dental, photocurable restorative material at the interface and thereby reduces gap formation between the cured dental liner composition and the cured direct dental, photocurable restorative material after which, a blue LED visible light-emitting dental curing light is applied to the restoration to complete photopolymerization of the direct restoration composite bulk.

6. The method of claim 5, wherein the infrared light causes the nanoparticles contained in the cured dental liner composition to locally emit blue light at a wavelength of near 460 nm.

7. The method of claim 5, wherein the infrared light causes the nanoparticles contained in the cured dental liner composition to locally emit violet light at a wavelength of near 400 nm.

8. The method of claim 5, wherein the subject in need thereof has a tooth decay, dental caries, or tooth erosion.

9. The method of claim 5, wherein the direct dental, photocurable restorative material is a restorative composite resin.

* * * * *